United States Patent [19]

Francis

[11] Patent Number: 4,831,013

[45] Date of Patent: * May 16, 1989

[54] 2-SUBSTITUTED-E-FUSED-[1,2,4]TRIAZOLO[1,5-C]PYRIMIDINES, PHARMACEUTICAL COMPOSITIONS, AND USES THEREOF

[75] Inventor: John E. Francis, Basking Ridge, N.J.

[73] Assignee: Ciba-Geigy Corporation, Ardsley, N.Y.

[*] Notice: The portion of the term of this patent subsequent to Dec. 15, 2004 has been disclaimed.

[21] Appl. No.: 20,055

[22] Filed: Feb. 27, 1987

Related U.S. Application Data

[63] Continuation-in-part of Ser. No. 913,173, Sep. 30, 1986, abandoned, which is a continuation-in-part of Ser. No. 841,986, Mar. 20, 1986, abandoned, which is a continuation-in-part of Ser. No. 782,234, Sep. 30, 1985, abandoned.

[51] Int. Cl.$^4$ .................. A61K 31/505; C07D 471/14; C07D 487/04; C07D 487/14
[52] U.S. Cl. ..................................... 514/23; 514/257; 514/267; 544/247; 544/251
[58] Field of Search .................. 544/251, 247; 536/35; 514/23, 267, 257

[56] References Cited

U.S. PATENT DOCUMENTS

| | | | |
|---|---|---|---|
| 3,045,015 | 7/1962 | Miller et al. | 544/251 |
| 3,053,844 | 9/1962 | Miller et al. | 544/251 X |
| 3,850,932 | 11/1974 | Kathawala | 544/251 |
| 4,053,600 | 10/1977 | Hardtmann et al. | 514/267 X |
| 4,087,423 | 5/1978 | Treuner et al. | 544/251 |
| 4,112,096 | 9/1978 | Vogt | 514/267 |
| 4,112,098 | 9/1978 | Vogt | 514/267 |
| 4,124,764 | 11/1978 | Treuner et al. | 544/251 |
| 4,128,644 | 12/1978 | Vogt | 514/267 |
| 4,164,578 | 8/1979 | Vogt | 514/267 X |
| 4,312,870 | 1/1982 | Yokoyama | 546/82 X |
| 4,463,007 | 7/1984 | Schlecker et al. | 544/251 X |
| 4,479,955 | 10/1984 | Yokoyama | 544/250 X |
| 4,524,146 | 6/1985 | Yokoyama | 514/273 |
| 4,560,689 | 12/1985 | Yokoyama | 514/250 |
| 4,585,772 | 4/1986 | Junge et al. | 514/267 X |
| 4,602,014 | 7/1986 | Yokoyama | 514/215 |
| 4,713,383 | 12/1987 | Francis et al. | 514/267 |

FOREIGN PATENT DOCUMENTS 0181282 5/1986 European Pat. Off. ............ 514/267
1670375 11/1970 Fed. Rep. of Germany.

OTHER PUBLICATIONS

Stanovnik et al., Synthesis, pp. 807–810 (1986).
H. Reimlinger, et al, Chem. Ber. 108:3799–3806 (1975).

*Primary Examiner*—Nicholas S. Rizzo
*Assistant Examiner*—Diana G. Rivers
*Attorney, Agent, or Firm*—Irving M. Fishman; JoAnn Villamizar

[57] ABSTRACT

Compounds of the formula

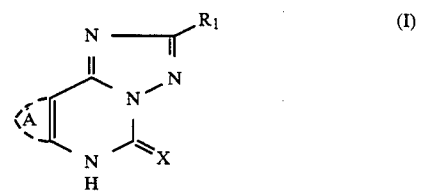

(I)

wherein $R_1$ is optionally substituted phenyl, pyridyl, thienyl, furyl, pyrrolyl, thiazolyl, or ribofuranosyl; X is oxygen, NR, or sulfur; R is hydrogen, lower alkyl, lower alkenyl, or lower alkynyl; and ring A is (a) an optionally substituted 5–8 membered monocycloalken-1,2-diyl; (b) an optionally substituted carbobicyclic ring of the formula

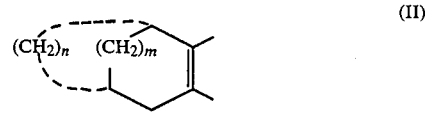

(II)

wherein n and m are each independently one or two; or (c) an optionally substituted 5–6 membered heterocycle having one or two heteroatoms, the atoms of which are selected from carbon, oxygen, nitrogen, and sulfur. Also disclosed are tautomers of the above and pharmaceutically acceptable salts; compositions thereof; and methods of using the compounds, tautomer, or salts.

45 Claims, No Drawings

2-SUBSTITUTED-E-FUSED-[1,2,4]TRIAZOLO[1,5-C]PYRIMIDINES, PHARMACEUTICAL COMPOSITIONS, AND USES THEREOF

FILE HISTORY CROSS REFERENCE

This application is a CIP of Ser. No. 913,173, filed Sept. 30, 1986; which is a CIP of Ser. No. 841,986, filed Mar. 20, 1986; which is a CIP of Ser. No. 782,234, filed Sept. 30, 1985, all abandoned.

The invention relates to new e-fused [1,2,4]triazolo[1,5-c]pyrimidines. More particularly, the inventive compounds have the formula

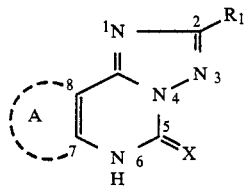

(Ia)

its tautomers and pharmaceutically acceptable salts wherein:

X is O, NR, or S; R is hydrogen, lower alkyl, lower alkenyl, or lower alkynyl;

$R_1$ is optionally substituted phenyl, pyridyl, thienyl, furyl, pyrrolyl, thiazolyl or ribofuranosyl; the $R_1$ optional substituents being lower alkyl, lower alkoxy, hydroxy, halogen, trifluoromethyl, hydroxy-lower alkyl, or amino; and ring A, inclusive of the two atoms it shares with the pyrimdine ring, is optionally substituted and selected from:

(A) a $C_5-C_8$ monocyclic cycloalkene;
(B) a bridged ring of the formula (II)

wherein n and m are each independently one to three; and (C) a heterocyclic ring selected from 2,5-dihydropyrrole, pyrrole, furan, oxazole, thiophene, piperidine, pyridine, pyrazine, pyrimidine, pyrazole, and imidazole;

the ring A optional substituents being selected from lower alkyl, lower alkoxy, hydroxy, halogen, trifluoromethyl, nitro, amino, carbamoyl, carbamoyl-lower alkyl, carboxy-lower alkyl, lower alkoxy-carbonyl, lower alkoxy carbonyl-lower alkyl, lower alkylthio, lower alkyl sulfinyl, lower alkyl sulfonyl, aryl, aryl lower alkyl, aryl lower alkoxy, aryl sulfonyl and tetrazolylalkyl;

the aryl group, as a separate group or as part of a larger group being (i) phenyl, hydroxy phenyl, lower alkyl phenyl, lower alkoxy phenyl or halophenyl; or (ii) pyridyl, thienyl, or furanyl, each of which is unsubstituted or further substituted by lower alkyl or halogen.

Also within the scope of the invention are the tautomeric forms of compounds within formula Ia typical of these tautomers are the structures below (Ib)

(Ic)

(Id)

(Ie)

which may arise spontaneously. Other tautomers which may spontaneously form (depending on the particular A ring) are also within the scope of the invention.

Triazolo[1,5-c]pyrimidines have been described in a number of references. U.S. Pat. Nos. 3,045,015 and 3,053,884 disclose primarily bicyclic compounds having an unsubstituted amino group in the two-position of the triazolo pyrimidine ring. However, some tricyclic rings are generically set forth such as those have a cyclohex-1-ene ring fused to the [e] face of the pyrimidine ring. These compounds are claimed as bronchodilators, respiratory stimulants, and antiarthritic agents. In addition, antibacterial, sedative, and hypotensive properties are disclosed. In J. Med. Chem. 17, 645–8 (1974), Novinson concludes that the compounds in U.S. Pat. No. 3,045,015 are active because they inhibit CAMP phosphodiesterase.

Shishoo, in J. Heterocyclic Chem. 18, 43–6 (1981), reports on the synthesis of angular tricyclics which are triazolopyrimidines having a heterocyclic fused to the [e] face of the pyrimidine ring. These are unsubstituted at the 2-position of the triazolopyrimidine ring system and have hydrogen, alkyl, aryl, or arylalkyl in place of the invention X.

Other heterocyclic rings fused to the [e] face of the [1,2,4] triazolo [1,5-c] pyrimidine ring system are mentioned in Huang et al, Chem. Pharm, Bull. 22 (8) 1938–9 (1974); Huang et al, Tetrahedron 31, 1363–7 (1975); Leonard and Wiemar; J.O.C. 39, 3438–40 (1974); Temple et al, U.O.C. 30, 3601–3 (1965); Sauter and Stanetty, Monatsh. Chem. 106, 1111–6 (1975); Brown and Shinozuka, Australian J. Chem. 34, 189–194 (1981); Bhat, Schram and Townsend, C. A. 95, 98200z (1981); Bhat and Townsend, J. C. S. Perkin I, 1981, 2387-2393; Schneller and Clough, J. Heterocyclic Chem. 1974, 975–7; Sangapure and Agasimundin, Indian J. Chem. B, 1980, 115–117; Saikachi, Matsuo and Matsuda, Yakugaku Zasshi 1969, 1434–9; and Petric, Tisler and Stanovnik, Montash. Chem. 114, 615–624 (1983). None of these compounds possess a carbonyl, thiono or imino at the triazolopyrimidine position 5. Further, only Saikachi et al mentions any compound having an aryl group at the 2-position of triazolopyrimidine. No biological properties are indicated.

Triazolopyrimidines having a phenyl ring fused at the [e] face, instead of the present invention ring A are mentioned in U.S. Pat. Nos. 4,463,007 and 4,053,600. Analogous pyrazolo pyrimidines are mentioned in U.S. Pat. Nos. 4,112,096; 4,112,098; 4,128,644; and 4,164,578. U.S. Pat. No. 4,585,772 discloses imidazopyrimidines or tetrahydropyrimidopyrimidines having a phenyl ring or a 6-membered heterocyclic having 5 carbons and nitrogen or 4 carbons and 2 nitrogens fused thereto. U.S. Pat. Nos. 4,087,423 and 4,124,764 disclose pyrazolotriazolo[4,3-c]pyrimidines. U.S. Pat. Nos. 4,479,955; 4,560,689; and 4,602,014 relate to pyrazolo pyridines having a partially saturated carbocyclic or heterocyclic ring fused to the pyridine ring.

Of all the compounds set out above, the only triazolo pyrimidines having indications of (beneficial) biological activity have the 2-position of the triazolopyrimidine ring system substituted with hydrogen an unsubstituted amino group, a carbonyl group, or lower alkyl. Therefore, it would be expected that one of these groups or a closely related one would be indespensable for useful biological properties to be present. Quite surprisingly, it has now been found that replacement of these groups with optionally substituted phenyl, pyridyl, thienyl, furyl, pyrrolyl, thiazolyl, or ribofuranosyl yields biologically active compounds as well. The new, useful compounds of the invention, especially when X is oxygen, affect benzodiazephine receptors, and, particularly when X is NR, affect adenosine receptors. Those compounds wherein X is S are primarily intermediates in the production of the compounds when X is oxygen or NR.

The benzodiazepine receptor (BR) agonists find utility as anxiolytics, CNS depressants, and anticonvulsants. BR inverse agonists (previously included with antagonists) elicit a response from the receptor, but opposite that which would result from an agonist, and as such find utility as anorectics, CNS stimulating agents, agents to increase cognitive ability, and to counteract the effects of benzodiazepines. True benzodiazepine antagonists merely block the receptor from benzodiazepines without eliciting a response therefrom. They are primarily useful in countering the effects of benzodiazepine. To the extent that the BR agonists elicit less of a response than benzodiazepines, they can also be used to counteract the effects of a benzodiazepine; however, due to the eliciting of an agonistic response from the receptor, it will necessarily be less efficacious than a similarly bound antagonist.

Adenosine agonists are primarily useful as antihypertensives. Adenosine antagonists find their primary utility as anti-asthmatic agents and in the treatment of bradyarrhythmias associated with clinical conditions such as myocardiac infarction and sleep apnea.

DETAILED DESCRIPTION OF THE INVENTION

The compounds of the invention are of the formula

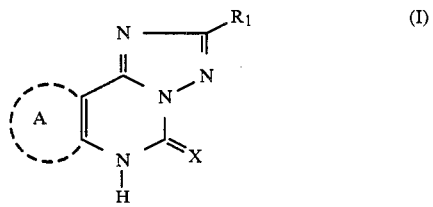

wherein
X is oxygen, NR, or S; R being hydrogen, lower alkyl, lower alkenyl, or lower alkynyl;

$R_1$ is (a) phenyl which is unsubstituted or substituted by lower alkyl, lower alkoxy, hydroxy, halogen, or trifluoromethyl; (b) furyl, thienyl, pyridyl, pyrrolyl, or thiazolyl, each of which is unsubstituted or substituted by lower alkyl, lower alkoxy, hydroxy, hydroxy-lower alkyl, halogen, or amino; or (c) β-D-ribofuranosyl;

ring A is (a) a 5–8 membered cycloalkene; (b) a bridged ring of the formula

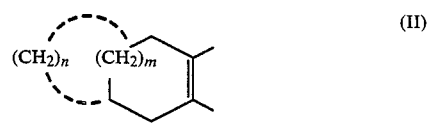

in which n and m are each independently one or two or three; or (c) a heterocycle selected from 2,5-dihydropyrrole, pyrrole, furan, oxazole, thiophene, piperidine, pyridine, pyrazine, pyrimidine, pyrazole, and imidazole;

each ring A being unsubstituted or substituted by lower alkyl, lower alkoxy, hydroxy, trifluoromethyl, nitro, amino, carbamoyl, carbamoyl lower alkyl, carboxy lower alkyl, lower alkoxy carbonyl, lower alkoxy carbonyl-lower alkyl, lower alkylthio, lower alkyl sulfinyl, lower alkyl sulfonyl, aryl, aryl-lower alkyl, aryl carbonyl, aryl lower alkoxy, or aryl sulfonyl; wherein aryl portion of the ring A substituent is selected from (a) phenyl, hydroxyphenyl, lower alkyl phenyl, lower alkoxyphenyl, and halophenyl; and (b) pyridyl, thienyl, and furyl, each of which is unsubstituted or substituted by lower alkyl or halogen; and tetrazolyl alkyl.

As used within this specification:
"Lower alkyl" means $C_1$–$C_7$, preferably $C_1$–$C_5$, more preferably $C_1$–$C_4$, alkyl.
"Lower alkenyl" means $C_2$–$C_7$, preferably $C_2$–$C_5$, more preferably $C_2$–$C_4$ alkenyl.
"Lower alkynyl" means $C_2$–$C_7$, preferably $C_2C_5$, more preferably $C_2$–$C_4$ alkynyl.
"Lower alkoxy" means $C_1$–$C_7$, preferably $C_2$–$C_5$, more preferably $C_2$–$C_4$ alkoxy.

Halogen and halo means fluorine, chlorine, and bromine. Unless apparent otherwise, reference made to "compounds" will also include the tautomers thereof. For purposes of consistency, when referring to the triazolopyrimidine bicyclic structure, the numbering system shown in structure Ia above will be used.

Preferred compounds for affecting the BR are those in which X is oxygen. For affecting the adenosine receptor (AR), the compounds wherein X is NR, more preferably NH or N-lower alkyl, are preferred.

$R_1$ is preferably (a) phenyl which is unsubstituted or substituted by one to three, preferably one, groups selected from lower alkyl (preferably methyl or ethyl), lower alkoxy (preferably methoxy or ethoxy), halogen (preferably fluorine or chlorine), hydroxy, and trifluoromethyl; or (b) furyl, pyridyl, pyrrolyl, or thiazolyl, more preferably furyl, pyridyl, or pyrrolyl, most preferably furyl or pyrrolyl, each of which is unsubstituted or mono or di-substituted (preferably unsubstituted or mono substituted) by lower alkyl (preferably methyl or ethyl), by lower alkoxy (preferably methoxy or ethoxy), by hydroxy, by hydroxy-lower alkyl (preferably hydroxy methoxy or hydroxy ethoxy), halogen (preferably fluorine or chlorine), or amino; or (c) β-D-ribofuranosyl. Of these $R_1$ groups, phenyl, furyl, pyrrolyl and pyridyl, either unsubstituted or substituted by fluorine or chlorine are more preferred. Unsubstituted phenyl, 2-, 3-, or 4-fluoro or chloro phenyl, and 2- or 3-furyl (preferably 2-furyl), 2-, 3- or 4-pyridyl (preferably 2-pyridyl, and 2- or 3-pyrrolyl (preferably 2-pyrrolyl) with the heterocyclic groups being unsubstituted or substituted by lower alkyl (preferably methyl or ethyl), hydroxy, or halogen (preferably fluorine or chlorine) are still more preferred. The $R_1$ phenyl groups are most advantageously ortho or meta, preferably ortho, substituted by fluorine or chlorine, preferably fluorine.

Ring A is cyclopentene, cyclohexene, cycloheptene cyclooctene; a ring of the formula

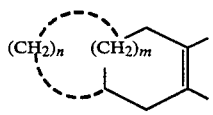

(II)

wherein the double bond is a fused side with the pyrimidine ring in formula Ia and n and m are each independently one, two or three; or a heterocycle selected from 2,5-dihydropyrrole, pyrrole, furan, oxazole, thiophene, piperideine, pyridine, pyrazine, pyrimidine, pyrazole, and imidazole, each ring A being optionally substituted.

Preferably, in the ring of formula II, m is one where n is three, or m and n are both two.

Preferably, the heterocyclic ring A is 2,5-dihydropyrrole, piperideine or pyridine. The piperideine ring is $\Delta^1$, $\Delta^2$, $\Delta^3$, or $\Delta^4$ piperideine, preferably $\Delta^3$ piperideine. The pyridine ring is preferably fused at the [c] or [d] side thereof to the pyrimidine ring in formula Ia. The piperideine ring is preferably unsubstituted or substituted as below, preferably N-substituted.

The ring A substituents are lower alkyl (preferably methyl or ethyl), lower alkoxy (preferably methoxy or ethoxy), hydroxy, trifluoromethyl, nitro, amino, carbamoyl, carbamoyl-lower alkyl (preferably carbamoyl methyl or carbamoyl ether), carboxy lower alkyl (preferably carboxy methyl or carboxy ethyl), lower alkoxy carbonyl (preferably methoxy- or ethoxy-carbonyl), lower alkoxy-carbonyl lower alkyl (preferably methoxy- or ethoxy-carbonyl methyl or ethyl), lower alkylthio (preferably methylthio or ethylthio), lower alkylsulfinyl (preferably methyl or ethyl sulfinyl), lower alkyl sulfonyl (preferably methyl or ethyl sulfonyl), aryl, aryl lower alkyl (preferably aryl-methyl or ethyl), aryl carbonyl, aryl lower alkoxy (preferably aryl methoxy, aryl ethoxy, aryl propoxy, or aryl butoxy, more preferably aryl methoxy or aryl ethoxy), or aryl sulfonyl; wherein the aryl group is phenyl, hydroxyphenyl, lower alkyl phenyl (preferably methyl or ethyl phenyl), lower alkoxy phenyl (preferably methoxy, ethoxy, or propoxy phenyl), halo phenyl pyridyl (preferably 2- or 4-pyridyl), thienyl, or furyl in which the pyridyl, thienyl and furyl of the "aryl" group is unsubstituted or further substituted by lower alkyl (preferably methyl or ethyl) or by halogen, and tetrazolylalkyl, preferably tetrazolylmethyl.

More preferable are the compounds wherein the ring A substituent is selected from lower alkoxy carbonyl lower alkyl, carbamoyl lower alkyl, carboxy lower alkyl, carbamoyl, aryl, aryl lower alkyl, aryl lower alkoxy, and aryl sulfonyl (preferences within each group and the definition of aryl being a in the preceding paragraph).

Still more preferred as the substituents of ring A are aryl lower alkyl (most preferably 2-picolyl, 4-picolyl, benzyl, 1-phenethyl), methoxy carbonyl methyl, carbamoyl methyl, phenyl sulfonyl, carbamoyl, and carboxy methyl.

In the above ring A substituents, phenyl is preferably unsubstituted or substituted by hydroxy (preferably 2- or 4-hydroxy) or by lower alkoxy (preferably 2- or 4-methoxy or ethoxy), while pyridyl, thienyl or furyl are preferably unsubstituted.

Especially preferred compounds of formula Ia are:

| | | | |
|---|---|---|---|
| (1) X = oxygen | $R_1$ = 2-fluorophenyl | A = cycloheptene | |
| (2) X = oxygen | $R_1$ = 2-fluorophenyl | A = N—(3-picolyl-$\Delta^3$-piperdeine | |
| (3) X = oxygen | $R_1$ = 2-fluorophenyl | A = cyclooctene | |
| (4) X = oxygen | $R_1$ = 2-fluorophenyl | A = N—methoxy-carbonyl-$\Delta^3$-piperideine | |
| (5) X = oxygen | $R_1$ = 2-fluorophenyl | A = cyclohexene | |
| (6) X = oxygen | $R_1$ = 2-fluorophenyl | A = N—benzyl-$\Delta^3$-piperdeine | |
| (7) X = NH | $R_1$ = furan-2-yl | A = cycloheptene | |
| (8) X = oxygen | $R_1$ = 2-fluorophenyl | A = N—ethoxy-carbonyl-methyl-$\Delta^3$-piperideine | |

Other important compounds will be found in the Examples.

The invention also relates to compounds of formula Ia wherein X is oxygen, NR, or S, with R being hydrogen or lower alkyl; $R_1$ being phenyl which is unsubstituted or substituted by one to three groups selected from lower alkyl, lower alkoxy, hydroxy, halogen, and trifluoromethyl; or furyl, thienyl, pyridyl, pyrrolyl, or thiazolyl, each optionally substituted by hydroxy, lower alkyl or halogen; and ring A is unsubstituted or substituted by one to three substituents selected from lower alkyl, lower alkoxy, aryl lower alkoxy, hydroxy, halogen, and trifluoromethyl, the "aryl" group being selected from unsubstituted or lower alkyl or halogen substituted phenyl, pyridyl, thienyl, and furyl and further selected from hydroxy phenyl and lower alkoxy phenyl.

Another preferred grouping are the compounds wherein X is oxygen and $R_1$ is optionally substituted phenyl, especially o- or m-halophenyl. An additional preferred class of compounds are those wherein $R_1$ is other than optionally substituted phenyl and X is NR; more preferably when $R_1$ is 2-furyl and X is NH.

Especially preferred compounds are those mentioned in the Examples.

Some of the compounds of the present invention can form acid addition salts, preferably pharmaceutically acceptable salts. Salts which are not pharmaceutically acceptable are suitable as intermediates for the preparation of the pharmaceutically acceptable salts or in the process of converting one compound of formula Ia into another of formula Ia. The acid addition salts are inorganic, exemplified by halide salts (such as chlorides), and sulfates, or organic which are typically exemplified by sulfonated or carboxylated lower alkyl or aryl groups. Some suitable organic salts include acetate, methanesulfonate, toluenesulfonate, fumarate, cinnamate, and benzoate.

The compounds of formula Ia wherein X is oxygen affect primarily the BR, while those wherein X is NR primarily influence the adenosine receptor. As such the oxo compounds (X=oxygen) exhibit anxiolytic and anticonvulsant effects and antagonism of the effects of benzodiazepine drugs (such as carbamazepine). The imino compounds (X is NR) are adenosine antagonists and consequently are primarily useful as antiasthmatic agents and central nervous system stimulating agents (they enhance cognitive ability).

Hence, the compounds of the invention, especially those wherein X is oxygen are useful in the treatment of nervous system disorders such as anxiety, convulsive conditions (i.e. epilepsy) and other disorders responsive to BR agonists or mixed agonist/antagonists.

The above effects are demonstrable in in vitro and in vivo tests using mammals, e.g. mice, rats, or monkeys, as test objects. The compounds can be administered enterally or parenterally, advantageously orally, subcutaneously, intravenously, or intraperitoneally n these tests, for example, in gelatin capsules or as aqueous solutions or suspensions. The dosage range for these tests is between about 0.1 and about 100 mg/kg/day, preferably between about 0.5 and about 50 mg/kg/day, advantageously between about 1 and 25 mg/kg/day. For the in vitro tests, the applied dose range is between about $10^{-5}$ and about $10^{-10}$ M concentration, preferably between about $10^{-7}$ and about $10^{-9}$ M.

For treatment of the conditions set forth above in mammals, such as human beings, the compounds are administered orally, intraperitoneally, or by inhalation in doses in the the range of 0.01 mg/kg to 500 mg/kg, preferably 0.1 mg/kg to 100 mg/kg, and most preferably about 10 mg/kg to about 30 mg/kg, body weight.

The benzodiazepine receptor binding properties indicative of the nervous system regulatory activity of said new compounds are determined in the receptor binding assay in vitro, e.g. similarly to that in Nature 266, 732 (1977) or Proc. Nat. Acad. Sci. USA 74, 3805 (1977). When tritiated flunitrazepam is used, the interaction of other drugs with said receptor can be readily assessed thus: Synaptosomal membranes from rat forebrain are incubated at 0°–5° for 30 minutes with 0.5 nM tritiated flunitrazepam and various concentrations of the test substance in a buffer medium maintained at pH 7.5. Solutions of various concentrations of test substance are prepared by dilution of a 4.2 mM stock solution in dimethylacetamide-ethanol (1:10) with 50 mM pH 7.5 Tris-HCl buffer. The membranes, containing the receptors with various amounts of tritiated flunitrazepam, are filtered onto glass fiber filters, which are then analyzed in a liquid scintillation counter. The concentration of the compounds of this invention, required to inhibit the specific binding of 0.5 nM of tritiated flunitrazepam by 50%, i.e. the $IC_{50}$, is determined graphically.

In vivo benzodiazepine receptor binding is determined essentially as described in Eur. J. Pharmacol. 48, 213 (1978) and Nature 275, 551 (1978).

Test compounds in a corn starch vehicle are administered orally or intraperitoneally to mice or rats. Thirty minutes later, $^3$H-flunitrazepam (2 nmoles/Kg in saline) is injected into the tail vein, and the animals are sacrificed 20 minutes after injection of the flunitrazepam. The brains are then assayed by determining radioactivity in a liquid scintillation counter for binding of the radioligand to the receptors. A decrease in the binding of $^3$H-flunitrazepam in the drug-treated animals (as compared with the binding observed in animals treated with vehicle alone) is indicative of benzodiazepine receptor binding by the test compound.

Anxiolytic effects are observed, for example, according to the Cook-Davidson conflict procedure, using male Wistar rats which are maintained at 80% of normal body weight by dietary-, but not water-restriction. They are trained to press a lever within a conditioning chamber, also containing a liquid dipper, a house light, a speaker and a grid-floor. The grids are connected to an electrical shock source and the chamber is situated in a sound-attenuated room in which a white noise-source is activated during testing, in order to mask any extraneous auditory cues. Each session of 47 minutes duration consists of two alternating schedules. The first is a Variable Interval (VI) schedule of 30 seconds, lasting for 5 minutes, during which a sweetened, condensed milk reinforcement is delivered following the first leverpress after an average of 30 minutes have elapsed, and a drug-induced decrement of this performance is taken as an indication of neurological deficit. Immediately following the VI-schedule both a 1000 Hz tone and a lightcue are activated, indicating the commencement of the second Fixed Ratio (FR) schedule, lasting for 2 minutes, wherein the milk reinforcement is delivered concomitant with an electric foot shock immediately following the tenth response, thereby establishing a conflict situation. The intensity of said shock ranges between 1.0–2.5 mA, varying with each animal, in order to adjust them to about 25–100 responses during this schedule over the entire session. A drug-induced enhancement of performance during the FR-schedule is taken as indication of antianxiety effects. This increased performance is measured by the increased number of electric foot shocks taken during six FR sessions lasting 2 minutes each.

Anticonvulsant effects are observed, for example in the standard Metrazole (pentylenetetrazole) and maximal electroshock tests for assessing anticonvulsant activity, e.g. orally in the rat.

Male Wistar rats (130–175 g) are fasted for 18 hours but allowed water as desired prior to testing. The test compound is administered in a cornstarch vehicle by oral intubation in a volume of 10 ml/Kg of body weight. One hour after administration of the test compound the animals are administered intravenously (caudal vein) a dose of 24 mg/Kg of Metrazole in water in a volume of 2.5 ml/Kg of body weight. The rats are immediately placed in plexiglass cylinders and observed for clonic seizures of at least 5 seconds duration during the next 60 seconds. The $ED_{50}$ is the dose at which half the animals are protected from Metrazole induced clonic seizures during the observation periods.

These and other methods are detailed more fully in Woods, J. Pharmacology and Experimental Therapeutics, Vol. 231, No. 3, 572–576 (1984).

Compounds which are preferred benzodiazepine agonists include, among others, those of formula Ia wherein X is oxygen, $R_1$ is 2-furanyl or optionally substituted phenyl and A completes a heptene ring or an optionally substituted, preferably N-benzyl substituted, 1,2,5,6-tetrahydro pyridine ring. Specific benzodiazepine agonists include the compounds of Examples 8, 10, 11, 12, and 25.

A preferred mixed benzodiazepine agonist/antagonist of the invention is, inter alia, 2(2-fluorophenyl)-7,8,9,10-tetrahydro-[1,2,4]triazolo[1,5-c]quinazoline-5-(6-H) one, set forth in Example 2.

The compounds of the invention, especially when X is imino or substituted imino, act as adenosine antagonists. Adenosine antagonism is assessed by determination of inhibition of adenosine activation of adenylate cyclase in vesicular preparations from guinea pig brains essentially as described in J. Neurochem. 22, 1031 (1974) and J. Neurochem. 38, 1437 (1982).

Specifically preferred adenosine antagonists of the invention are 5-amino-2-(2-furyl)-7,8,9,10-tetrahydro-[1,2,4]triazolo[1,5-c]quinazoline methanesulfonate and 5,6-dihydro-2-(2-furyl)-5-iminopyrido[3,2-e][1,2,4]triazolo[1,5-c]pyrimidine methanesulfonate.

The compounds of formula Ia (their tautomers and pharmaceutically acceptable salts) are formulated into pharmaceutical compositions comprising an effective amount of the triazolopyrimidine compounds of formula Ia or a pharmaceutically acceptable salt thereof in combination with conventional excipients or carriers suitable for either enteral or parenteral, such as oral, bronchial, rectal or intravenous, administration. Preferred are tablets, dragees and gelatin capsules comprising the active ingredient together with (a) diluents, e.g., lactose, dextrose, sucrose, mannitol, sorbitol, cellulose, calcium phosphates and/or glycine, (b) lubricants, e.g. silica, talcum, stearic acid, its magnesium or calcium salt and/or polyethyleneglycol; for tablets also, (c) binders, e.g. magnesium aluminum silicate, starch paste, gelatin, tragacanth, methylcellulose, sodium carboxymethylcellulose and/or polyvinylpyrrolidone; if desired, (d) disintegrants, e.g. starches, agar, alginic acid or its sodium salt, or effervescent mixtures and/or, (e) absorbents, colorants, flavors and sweeteners. Dragee or tablet cores may be provided with suitable coatings, which may be resistant to gastric juices. Coating solutions are, for example, concentrated aqueous sugar solutions, which may contain gum arabic, polyvinylpyrrolidone, polyethylene glycol, talcum and/or titanium dioxide. Resistant coatings are obtained with lacquer solutions in organic solvents, such as shellac, acetylcellulose phthalate or hydroxypropylmethylcellulose phthalate in ethanol and the like. Dyestuffs or pigments may be added for identification of brand name and dose. Capsules are either made from hard gelatin, or they are soft, closed capsules made from gelatin and a softener, e.g., glycerin or sorbitol. The hard capsules contain either uncompressed powder mixtures, e.g. those mentioned under (a) and (b), or granulates similar to those used for tablets. In the soft capsules said active ingredients are preferably dissolved or suspended in suitable liquids, such as fatty oils, paraffins or polyethylene glycols. Suppositories are advantageously solid, fatty emulsions or suspensions, containing the active ingredient, for example, in natural or synthetic triglycerides, paraffins, waxes and/or polyethylene glycols.

Compositions for parenteral administration are preferably aqueous solutions or suspensions of said active substances, but also oily solutions or suspensions of said active substances, but also oily solutions or suspensions thereof, e.g., in natural or synthetic fatty oils, such as sesame oil or ethyl oleate, in suitable ampules.

Bronchial compositions are preferably aerosol sprays and may be administered from a dispenser such as is described in U.S. Pat. Nos. 4,292,966, 4,174,712, and 4,137,914. The active ingredient is mixed with a propellant such as a hydrocarbon, chlorofluorocarbon mixture, or carbon dioxide.

The compositions may be sterilized and/or contain adjuvants, such as preserving, stabilizing, wetting or emulsifying agents, solution promoters, salts for regulating the osmotic pressure and/or buffers. They may also contain other therapeutically valuable substances, and are prepared according to conventional mixing, granulating or coating methods respectively. They may contain from about 10 to 95%, preferably from about 20 to 70% of the active ingredient. Individual unit dosages thereof for a mammal of about 50–70 Kg weight may contain preferably between about 10 and 200 mg., advantageously about 20 to 100 mg of said active ingredients.

Benzodiazepine antagonism is measured by the antagonism of the diazepam-induced rotorod deficit in the rat. Diazepam (30 mg/kg/ip) and test compound are administered 30 minutes and 1 hour, respectively, before the test.

In the maximal electroshock precedure for assessing anticonvulsant activity in rats, seizures are induced by applying 150 mA of electric current for 0.2 seconds through corneal electrodes two hours after oral administration of test compound. The $ED_{50}$ is the dose at which half the animals are protected from electroshock induced seizures during a 5 second observation period.

The pharmacological benzodiazepine agonist and/or antagonist profile of the compounds of the invention can also be determined by measuring their effect in a rat brain membrane preparation on the displacement of $^3$H-flunitrazepam in the presence or absence of gamma-aminobutyric acid (GABA), or on the enhancement of $^3$H-muscimol binding by etazolate, or on the binding by etazolate, or on the binding of $^{35}$S-butyl bicyclophosphorothionate (TBPS).

The compounds of the present invention can be prepared by methods known in the art. In addition, they can be prepared by the following methods.

The compounds of formula Ia wherein X is oxygen can be prepared by (a) reacting a compound of the formula

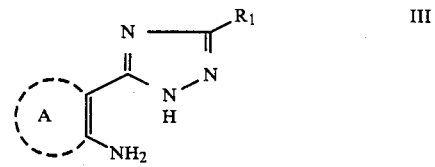

III with a reactive derivative of carbonic acid, which includes esters, amides, and anhydrides of carbonic acid. Included here are phosgene, diethylcarbonate, ethylcarbamate and trichloromethyl chloroformate.

The compounds of formula III can be prepared by treating a reactive intermediate of an alpha,beta-cyclic-beta-amino acrylic acid, such as tetrahydro isatoic anhydride, with a compound of the formula

IVa

Alternatively, compounds of formula III can be prepared from compounds of the formula

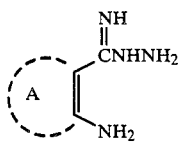

and

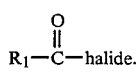

The alpha,beta-cyclic-beta-amino acrylic acid intermediates may also be of the formula

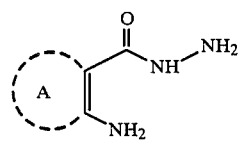

which are reacted with

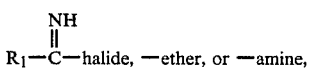

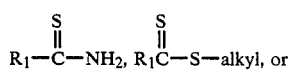

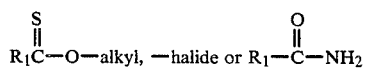

or halide, or the corresponding acid anhydride to yield a compound of formula III. Compounds of formula VI can be prepared from the corresponding acid of formula VII

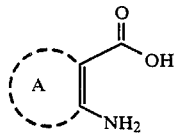

by esterification, followed by reacting with hydrazine.

Compounds of formula III can also be obtained by hydrolyzing the compounds of formula Ia by treatment thereof with alkali metal hydroxide.

The compounds of formula III can further be prepared by selective ring closure in a compound of the formula

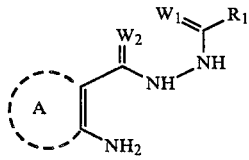

wherein one of $W_1$ and $W_2$ is oxygen and the other is NH or wherein $W_1$ and $W_2$ are both NH.

(b) ring closure in a compound of the formula

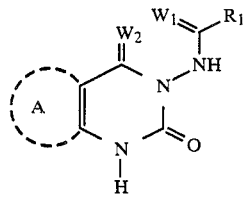

where $W_1$ and $W_2$ are as defined in process (a), by treatment thereof with a base, preferably a tertiary amine such as triethylamine or piperidine. The compound of formula IX is prepared by selective ring closure of a compound of formula VIII (defined above).

(c) reacting a compound of formula VIII with a reactive derivative of carbonic acid and a base.

(d) treating a compound of the formula

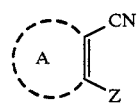

wherein Z is isocyanato,

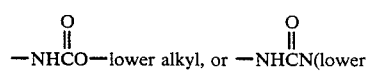

alkyl)$_2$ with a hydrazide of the formula

The compounds of formula X where Z is

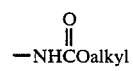

can be readily prepared by reacting

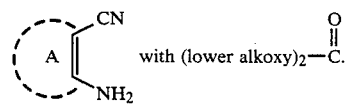

(e) treating a compound of the formula

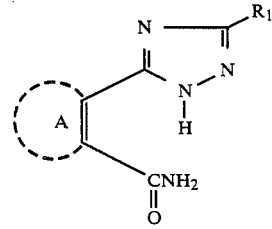

with an oxidizing agent followed by ring closure.

(f) hydrolyzing a compound of the formula

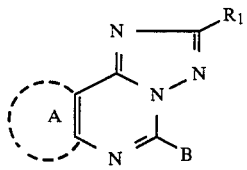

wherein B is halo or alkoxy.

(g) treating a compound of formula Ia wherein X is sulfur with a hypohalite salt.

(h) treating a compound of formula Ia wherein X is NR with aqueous acid.

Compound of formula Ia wherein X is S can be prepared analogously to the X=oxygen (hereinafter the "oxo" compounds) compounds using the compounds set forth except that the carbonyl which ultimately includes X in the oxo compounds is replaced by thiocarbonyl. Thus, replacement of the carbonic acid derivative in process a above with the corresponding thio carbonic acid yields the compounds having X=S ("thiono" compounds). The same can be said regarding process c and d. Where isocyanates are indicated for the oxo compound synthesis isothiocyates will yield the corresponding thiono compounds.

Compounds of formula Ia wherein X is NR can be prepared by (i) reacting a compound of formula III, as defined in process (a) above, with cyanogen halide followed by cyclization or reacting a compound of formula III with cyanamide or a reactive imino carbonyl derivative.

(j) ring closure as in process (b), but using a compound of the formula

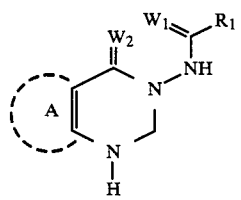

wherein one of $W_1$ and $W_2$ is oxygen and the other NH, or $W_1$ and $W_2$ are both NH, instead of the compound of formula IX, preferably by treatment thereof with ammonia. The compound of formula XIV is prepared by selectively cyclizing a compound of the formula

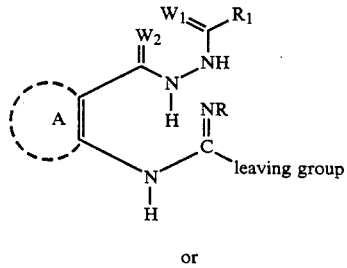

or

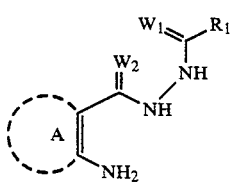

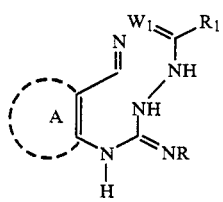

The compounds of formula XV are prepared from those of formula XVI. the reaction of compounds of formula XVI to compounds of Formula XIV requires the presence of a reactive imino carbonic acid derivative, a cyanogen halide or cyanamide. The compounds of formula XVII are prepared from the reaction of a compound of the formula

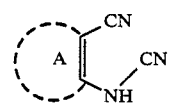

with a hydrazine of formula XI.

(k) by doubly cyclizing a compound of formula XV or XVI or XVII, the reaction of the compound of formula XVI being in the presence of a cyanogen halide or cyanamide or a reactive imino carbonic acid derivative.

(l) cyclizing a compound of the formula

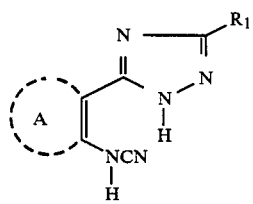

which is prepared from a compound of formula III by reaction thereof with cyanogen halide.

(m) reacting a compound of formula XIII wherein B is halo or a compound formula Ia wherein X is thiono with an amine of the formula $RNH_2$ (n) reacting a compound of the formula

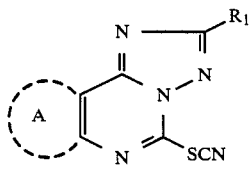

with an amine of the formula $RNH_2$. The compounds of formula XIX are obtained by reacting the corresponding thiono compounds with cyanogen halide in the presence of base.

(o) reacting a compound of the formula

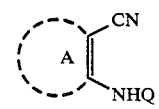

wherein Q is —CN or

group with a hydrazide of formula XI.

(p) or in any event, by converting one claimed compound into another or by converting a salt into a claimed compound or a claimed compound into a salt, such as

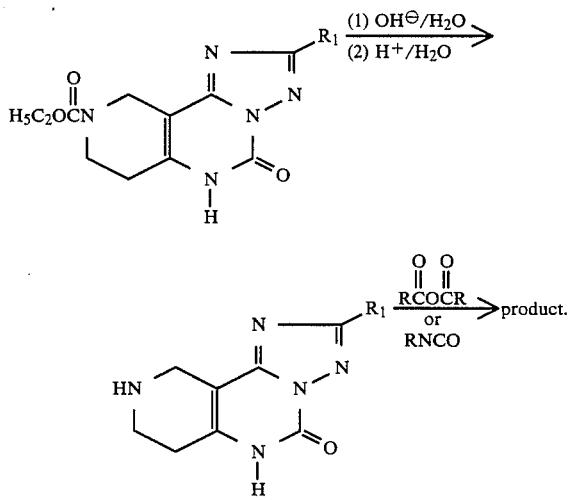

In process variant a, a compound of formula VIII is converted to a compound of formula III by reaction thereof with a base, preferably a tertiary amine or ammonia.

In process variant b, a compound of formula VIII is converted to a compound of formula IX by reaction thereof with a reactive derivative of carbonic acid as that term is defined in process a. Use of the corresponding reactive derivative of thiocarbonic acid will yield the corresponding thiono compound and use of the corresponding reactive derivative of imino carbonic acid (which includes cyanamide) will result in the corresponding imino compound of formula XIV.

In process c, the reactive derivative of carbonic acid and the base are preferably those in variants a and b.

In process variant d, the reaction takes place preferably in a solvent, such as an ether solvent, for example dioxane, or an alcohol solvent, for example 2-methoxyethanol, or a liquid amide such as dimethylacetamide.

When Z represents isocyanate or —NHC(=O)O lower alkyl, the reaction is conducted in the presence of a base such as a teriary amine, for example N-methylmorpholine, triethylamine, and, especially, tripropylamine. The compounds having formula X wherein Z represents isocyanato may be converted into the corresponding compounds wherein Z represents —NHC-(=O)O—lower alkyl by treatment with a lower alkanol such as ethanol. Lower alkyl is preferably methyl or ethyl.

The compounds having formula X wherein Z represents —NH(C=O)O—lower alkyl may also be formed by treating an, alpha-beta-cyclic eneamino nitrile with lower alkyl chloroformate for example ethyl chloroformate.

The compounds having formula X wherein Z represents NHC(=O)-di-lower-alkyl may be formed by treating the appropriate O-isocyanatocyclic ene nitrile with a di-lower-alkylamine such as diethylamine.

The preferred solvents when Z represents isocyanato are ether solvents, especially dioxane. The preferred solvents when XH represents —NHC(50 O)O—lower alkyl or NHC(=O)N—di—lower alkyl are alcohol solvents, especially 2-methoxyethanol. A preferred solvent in either case is a liquid amide, such as dimethyl acetamide. The reaction is preferably conducted at temperatures of 0° to 250° C., preferably 20° to 150° C.

In the above, replacement of cyanato and carbonyl groups by thiocyanato and thiocarbonyl groups, respectively, in Formula X will yield the corresponding compounds wherein X is sulfur.

The starting compounds of process d, i.e.

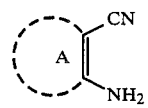

wherein A is a bridged group of formula II can be prepared by the Thorpe-Ziegler reaction as detailed in The Chemistry of Cyclic Eneaminonitriles and O-aminonitriles, ed. E. C. Taylor, Interscience (1970), New York, pp. 11–56. A typical reaction scheme is

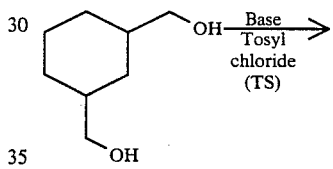

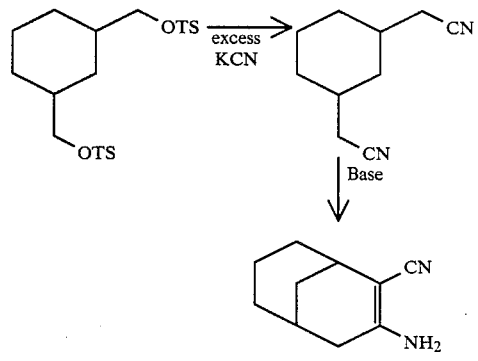

In process variant e, the oxidizing agent may be, for example, lead tetraacetate or a hyponalite. The hypohalite is preferably an alkali metal hypohalite such as sodium hypochlorite or sodium hypobromite. The amide function is believed to undergo the first stage of the Hofmann reaction (Ber. 14, 2725 (1881), forming the isocyanate which then reacts with the free NH of the triazole.

In process variant f, a 5-halo, lower alkoxy or aryl lower alkoxy substituted e-fused [1,2,4]triazolo[1,5-c]pyrimidine is hydrolyzed. The hydrolysis is preferably carried out with aqueous alkali.

The 5-halo compounds may be prepared be reacting a compound of formula Ia wherein X represents O with a reactive halide such as phosphoryl chloride or phosphorous pentachloride, most preferably phenylphosphonic dichloride, with or without an inert solvent.

The 5-lower alkoxy or 5-aryl-alkoxy compounds may be prepared from the 5-halo compounds by treatment with the appropriate alcohol in the presence of a base, preferably a tertiaryamine.

In process variant g, the hypohalite salt is preferably the same as that in process variant e.

In process variant (i), the cyanogen halide is preferably cyanogen chloride or cyanogen bromide, more preferably cyanogen bromide. The hydrohalide formed in the reaction may be neutralized with base, suitably triethylamine, pyridine, sodium hydride. The cyclization step is catalyzed by mineral acids or by bases, such as hydrohalides or trialkylamines, respectively.

In process variant j, procedures analogous to those in variant a are used. The related o-cyanimidobenzonitriles, which replace instant ring A with a benzene ring are described by Wentrup in Tetrahedron, 27, 367 (1971) and by Bedford in J. Chem. Soc. 1633 (1959). The compound of formula Xa can also be converted directly into a compound of formula Ia by the described reaction, structure XVII being an intermediate therein, as in process variant f.

In process variant n, the reaction is carried out in an aprotic solvent, preferably at or near room temperature. The compounds of Formula XIX can be prepared from the corresponding thiono compounds of Formula Ia by treatment thereof with cyanogen halide, preferably cyanogen bromide, in the presence of base, such as sodium hydride.

Having generally described the invention, a more complete understanding can be obtained by reference to certain specific examples, which are provided herein for purposes of illustration only and do not limit the claims unless otherwise specified. Within the Examples, numbering of the ring systems is in accordance with the generally accepted rules of nomenclature.

EXAMPLE 1

A mixture of 3-(5-aminoimidazol-4-yl)-5-phenyl-1,2,4-triazole (8.5 g), trichloromethylchloroformate (7.0 g) and dioxane (400 mL) is stirred under nitrogen at 20° for 64 hours. To this is added triethylamine (5.15 mL) and the mixture is stirred at 20° for 4 hours, collected, washed with water and air dried. It is recrystallized from dimethylformamide-ether, digested with warm methanol, filtered, washed with ether and oven dried at reduced pressure to afford 2-phenyl-[1,2,4]triazolo[5,1-i]purin-5-(6H)one as a hemihydrate, m.p. above 300°.

The starting material is prepared in the following way:

A mixture of 6-hydrazinopurine, prepared as described by Montgomery and Holum, J. Amer. Chem. Soc. 79, 2187 (1957), (13.5 g) diphenyl ether (300 mL), 1 molar p-toluenesulphonic acid in isopropanol (10 mL) and trimethyl orthobenzoate (81 mL) is stirred at 180° in an appratus containing a solvent removal trap over 2.5 hours. The mixture is cooled, diethyl ether (400 mL) added and the resulting solid stirred in hot ethanol (200 mL) for several minutes and collected. This product (12.1 g) is heated with 2.5 molar HCl in isopropanol for 18 hours at 60°, cooled, collected, washed with a little cold water and stirred 5 minutes with 10 mL of 5% aqueous sodium carbonate solution to afford the above triazole, m.p. 278°–280° C. The hydrochloride of this product melts in the range 324° to 326° C.

EXAMPLE 2

The ethyl carbamate of 3,4,5,6-tetrahydroanthranilonitrile (10 g), o-fluorobenzhydrazide (7.94 g), tri-n-propylamine (6.9 ml) and 2-methoxyethanol (170 mL) is stirred at reflux for 18 hours under nitrogen. It is cooled to room temperature and the precipitate which forms is collected, washed with ethanol and dried in vacuo. The product, 2-(2-fluorophenyl)-7,8,9,10-tetrahydro-[1,2,4]triazolo[1,5-c]quinazolin-5(6H)one melts in the range 266 to 268° C.

The ethyl carbamate is prepared in the following way:

To a solution of sodium (43.5 g) dissolved in absolute ethanol (550 mL) is added 3,4,5,6-tetrahydroanthranilonitrile (29.1 g) and diethylcarbonate (280 mL) and the whole stirred at reflux under nitrogen for 2 hours. The solution is ice cooled and glacial acetic acid (145 mL) added cautiously followed by water (600 mL). The aqueous layer is extracted with ether several times and the extract dried over magnesium sulphate and concentrated to dryness at reduced pressure to afford an oil which gradually crystallizes. It is used without further purification (42.2 g).

EXAMPLE 3

When 2-furoic acid hydrazide is substituted for o-fluorobenzhydrazide in Example 2, 2-(2-furyl)-7,8,9,10-tetrahydro[1,2,4]triazolo[1,5-c]quinazolin-5(6H)one is obtained as a white solid, m.p. 327°–330°, with decomposition, in 60% yield.

EXAMPLE 4

A mixture of the ethyl carbamate of 3,4,5,6-tetrahydroanthranilonitrile (8.5 g), o-methylaminobenzhydrazide (7.2 g) and 1-methyl-2-pyrrolidone (80 mL) is stirred under nitrogen at reflux for 16 hours, cooled, diluted with water (300 mL) and the precipitated solid collected, washed with water and pressed dry on the filter. It is washed with ether (100 mL) and oven dried. The free base is suspended in methanol and treated with an equimolar quantity of methanesulphonic acid. The methanesulphonate salt of 2-(2-methylaminophenyl)-7,8,9,10-tetrahydro-[1,2,4]triazolo[1,5-c]quinazolin-5(6H)one crystallizes, m.p. 257°–260°, in 36% yield.

EXAMPLE 5

When 3-chlorobenzhydrazide is substituted for o-fluorobenzhydrazide in Example 2, 2-(3-chlorophenyl)-7,8,9,10-tetrahydro-[1,2,4]triazolo[1,5-c]quinazolin-5-(6H)one is obtained and purified by recrystallization from 2-methoxyethanol, m.p. 342°–346° dec. in 50% yield.

EXAMPLE 6

A mixture of o-fluorobenzhydrazide (8.56 g) 1-amino-2-cyano cyclopenten-1-yl ethyl carbamate (10 g, prepared as described by House et al, J.A.C.S. 84, 3139–3147 (1962)) 2-methoxyethanol (185 mL) and tri-n-propylamine (7.4 mL) is stirred under nitrogen at reflux for 20 hours, cooled and treated gradually with water to induce crystallization. It is collected, washed with water, dried and recrystallized from ethanol to afford 8,9-dihydro-2-(2-fluorophenyl)-7H-cyclopenta[e][1,2,4]triazolo[1,5-c]pyrimidin-5(6H)one melting in the range 251° to 253°, in 68% yield.

EXAMPLE 7

When 2-furoic acid hydrazide is substituted for o-fluorobenzhydrazide in Example 6,8,9-dihydro-2-(2-furyl)-7H-cyclopenta[e][1,2,4]triazolo[1,5-c]pyrimidin-5-(6H)one is obtained, m.p. 197°-299° in 53% yield.

EXAMPLE 8

A mixture of the ethylcarbamate of N-benzyl-3-cyano-4-amino-$\Delta^3$-piperideine (8.2 g), o-fluorobenzhydrazide (4.43 g), 2-methoxyethanol (96 mL) and tri-n-propylamine (3.9 mL) is stirred at reflux under nitrogen for 42 hours. It is cooled and the precipitated solid collected, washed with ethanol, dried and rrecrystallized from 2-methoxyethanol to afford pure 9-benzyl-2-(2-fluorophenyl)-7,8,9,10-tetrahydropyrido[3,4-e][1,2,4]triazolo [1,5-c]pyrimidin-5(6H)one, melting in the range 256° to 259°. When treated with an equimolar quantity of methanesulphonic acid in methanol, the free base is converted to the methanesulphonate salt (38%) m.p. 306°-309° after recrystallization from 1:1 dimethylacetamide-methanol mixture.

The above ethyl carbamate derivative is prepared by the method described in Example 2 from N-benzyl-3-cyano-4-amino-$\Delta^3$-piperideine (Taylor et al, Tetrahedron 23, 855-890 (1967)) and is obtained as an oil in 94% yield.

EXAMPLE 9

When the ethylcarbamate of Example 8 is replaced by N,N-dicarbethoxy-3-cyano-4-amino-$\Delta^3$-piperideine, 9-carbethoxy-2-(2-fluorophenyl)-7,8,9,10-tetrahydropyrido[3,4-e][1,2,4]-triazolo[1,5-c]pyrimidin-5-(6H)one is obtained, m.p. 307°-311° with decomposition, in 46% yield.

The bis-urethane starting material is prepared in the following way: To a solution of sodium ethoxide in ethanol, prepared from 40.2 g of sodium dissolved in 500 mL of absolute ethanol, is added 3-cyano-4-amino-$\Delta^3$-piperidiene (26.9 g, prepared as described by Bachmann and Barker, J. Amer. Chem. Soc. 69, 1535 (1947)) and the whole refluxed 1 hour under nitrogen. Diethyl carbonate (205 mL) is added and the whole stirred at reflux for 2 hours under nitrogen, cooled to room temperature and glacial acetic acid (20 mL) followed by water (1.3 L) is added cautiously. The resulting solution is extracted with ether (4×500 mL) and the ether extracts concentrated to about 600 mL, dried over magnesium sulphate and concentrated at reduced pressure to a syrup. Trituration with ether causes precipitation of some solid and concentraton of the ethereal mother liquor yields a second crop of product, m.p. 170°-172°, suitable for further word. The yield is 68%.

EXAMPLE 10

A mixture of the ethyl carbamate of N-benzyl-3-cyano-4-amino-$\Delta^3$-piperideine (5.3 g), benzhydrazide (2.53 g), dimethylacetamide (70 mL) and diisopropylethylamine (0.5 mL) is stirred at reflux under nitrogen for 18 hours. It is concentrated to dryness at reduced pressure, triturated with isopropanol and the resulting solid collected, dried and recrystallized from 2-methoxyethanol to afford pure 9-benzyl-2-phenyl-7,8,9,10-tetrahydropyrido[3,4-e][1,2,4]triazolo[1,5-c]pyrimidin-5(6H)one, m.p. 257°-259° (72% yield).

EXAMPLE 11

A mixture of the ethylcarbamate of N-benzyl-3-cyano-4-amino-$\Delta^3$-piperideine (10 g), p-fluorobenzhydrazide (5.41 g) and 1-methyl-2-pyrrolidone (80 mL) is stirred at reflux under nitrogen for 20 hours. It is evaporated at reduced pressure to remove most of the solvent, then diluted with isopropanol (100 mL) and stirred one-half hour. The precipitated product is collected, washed with isopropanol and dried. It is converted to the p-toluenesulphonate salt by treatment with an equimolar amount of p-toluenesulphonic acid in methanol. The salt is suspended in 2-methoxyethanol, filtered and converted back to the free base in dilute ammonium hydroxide, in 42% yield. The pure 9-benzyl-2-(4-fluorophenyl)-7,8,9,10-tetrahydropyrido-[3,4-e][1,2,4]triazolo[1,5-c]pyrimidin-5(6H)one melts in the range 252° to 256°.

EXAMPLE 12

When 4-chlorobenzhydrazide is substituted for benzhydrazide in Example 10, 9-benzyl-2-(4-chlorophenyl)-7,8,9,10-tetrahydropyrido [3,4-e][1,2,4]triazolo[1,5-c]pyrimidin-5(6H)one is obtained melting in the range 250° to 256° in 54% yield.

EXAMPLE 13

When 3-fluorobenzhydrazide is substituted for p-fluorobenzhydrazide in Example 11, 9-benzyl-2-(3-fluorophenyl)-7,8,9,10-tetrahydropyrido[3,4-e][1,2,4]triazolo[1,5-c]pyrimidin-5(6H)one is obtained and purified as the methanesulphonate salt. After recrystallization from dimethylacetamide-methanol, it melts in the range 299;1 ° to 302° and is obtained in 30% yield.

EXAMPLE 14

A mixture of N,N'-dicarbethoxy-3-cyano-4-amino-$\Delta^3$-piperideine (18.5 g), 2-furoic acid hydrazide (8.73 g) 2-methoxyethanol (220 mL) and tri-n-propylamine (90 mL) is refluxed under nitrogen for 18 hours. It is cooled, concentrated at reduced pressure to a thick slurry, diluted with water (500 mL), stirred for 1 hour and the solid colleced, washed with methanol and air dried. The 9-carbethoxy-2-(2-furyl)-7,8,9,10-tetrahydropyrido[3,4-e][1,2,4]triazolo[1,5-c]pyrimidin-5(6H)one thus obtained, (11.1 g) decomposes in the range of 316° to 320°.

EXAMPLE 15

A suspension of 9-carbethoxy-2-(2-fluorophenyl)-7,8,9,10-tetrahydropyrido[3,4-e][1,2,4]triazolo[1,5-c]pyrimidin-5(6H)one from Example 9 (15,4 g) in 2-methoxyethanol (145 mL) and 4 normal aqueous sodium hydroxide (73 mL) is stirred under nitrogen at 120° for 16 hours. The cooled reaction mixture is gradually brought to pH 6 with dilute hydrochloric acid under stirring. The solid material is collected, recrystallized from 2-methoxypropanol and dried in vacuo at 100° for 20 hours. The pure 2-(2-fluorophenyl)-7,8,9,10-tetrahydropyrido[3,4-e][1,2,4triazolo[1,5-c]-pyrimidin-5(6H)one thus obtained melts in the range 254° to 257° (68% yield).

EXAMPLE 16

By the method described in Example 15, 2-(2-furyl)-7,8,9,10-tetrahydropyrido[3,4-e][1,2,4]triazolo[1,5-c]pyrimidine-5(6H)one is obtaned from the urethane of

EXAMPLE 17

To a solution of 2-(2-fluorophenyl)-7,8,9,10-tetrahydropyrido[3,4-e][1,2,4]triazolo[1,5-c]pyrimidin-5(6H)one (1.03 g, Example 15), triethylamine (0.9 mL) and 1-methyl-2-pyrrolidinone (18 mL) under nitrogen and magnetic stirring in an ice bath is added benzoyl chloride (0.83 g). It is stirred at room temperature for 48 hours, then diluted with water and extracted with ethyl acetate. The insoluble material is collected, washed with ether and air dried to afford pure 9-benzoyl-2-(2-fluorophenyl)-7,8,9,10-tetrahydropyrido[3,4-c][1,2,4]triazolo[1,5-c]pyrimidin-5-(6H)one, in 83% yield, melting at 342° to 344°.

EXAMPLE 18

A mixture of 2-(2-fluorophenyl)-7,8,9,10-tetrahydropyrido[3,4-e][1,2,4]triazolo[1,5-c]pyrimidin-5(6H)one (0.57 g, Example 15) and phenylacetylchloride (3 mL) is heated under nitrogen at 120° for 4 hours. The mixture is diluted with ether (30 mL) and the solid collected, washed with ether and air dried to afford pure 9-phenylacetyl-2-(2-fluorophenyl)-7,8,9,10-tetrahydropyrido[3,4-e][1,2,4]triazolo[1,5-c]pyrimidin-5(6H)one, m.p. 310°–313°, in 85% yield.

EXAMPLE 19

A mixture of 2-(2-fluorophenyl)-7,8,9,10-tetrahydropyrido[3,4-e][1,2,4]triazolo[1,5-c]pyrimidin-5(6H)one (0.57 g, Example 15) and phenylisocyanate (3 mL) is heated at 120° for 4 hours, cooled and the resulting solid triturated with ether (30 mL), filtered, washed with ether and dried. the pure 9-phenylureido-2-(2-fluorophenyl)-7,8,9,10-tetrahydro pyrido[3,4-e][1,2,4]triazolo[1,5-c]pyrimidin-5(6H)one is thus obtained, m.p. 291°–293°, in 89% yield.

EXAMPLE 20

A mixture of the ethylcarbamate of N-methyl-3-cyano-4-amino-$\Delta^3$-piperideine (14.6 g), o-fluorobenzhydrazide (10.78 g), tri-n-propylamine (9.5 mL) and 2-methoxyethanol (230 mL) is stirred at reflux under nitrogen for 66 hours, cooled and concentrated to a small volume at reduced pressure. The residue is triturated with isopropanol and the resulting solid collected, washed with methanol and dried. The solid is taken up in methanol, treated with an equimolar quantity of methanesulphonic acid and the resulting salt collected and dried in vacuo to afford pure 2-(2-fluorophenyl)-9-methyl-7,8,9,10-tetrahydropyrido-[3,4-e][1,2,4]triazolo[1,5-c]pyrimidin-5(6H)one methanesulphonate, m.p. 285°–287° in 41% yield.

The starting carbamate is prepared by the method described in Example 2 from N-methyl-3-cyano-4-amino-$\Delta^3$-piperideine, prepared as described by Cologne et al, Bull, Soc. Chim. France, 1963, 2264–2270, in 86% yield.

EXAMPLE 21

When the ethyl carbamate of N-ethyl-3-cyano-4-amino-$\Delta^3$-piperideine is substituted for the N-methyl compound of Example 20, 9-ethyl-2(2-fluorophenyl)-7,8,9,10-tetrahydropyrido[3,4-e][1,2,4]triazolo[1,5-c]pyrimidin-5(6H)one methanesulphonate is obtained, m.p. 284°–286°, in 48% yield.

The ethyl carbamate is prepared by the method described in Example 2 from N-ethyl-3-cyano-4-amino-$\Delta^3$-piperideine, prepared as described by Cologne et al, Bull. Soc. Chim. France, 1963, 2264–2270, in 81% yield.

EXAMPLE 22

When the ethyl carbamate of N-isopropyl-3-cyano-4-amino-$\Delta^3$-piperideine is substituted for the N-methyl compound of Example 20, 2-(2-fluorophenyl)-9-isopropyl-7,8,9,10-tetrahydropyrido[3,4-c][1,2,4-]triazolo[1,5-c) pyrimidin-5(6H)one methanesulphonate is obtained, m.p. 300°–303° in 62% yield.

The ethyl carbamate used as sftarting material is prepared from N-isopropyl-3-cyano-4-amino-$\Delta^3$-piperideine as described in Example 2. This amino compound is prepared from N-isopropyl bis($\beta$-cyanoethyl)amine as described by Cologne et al, Bull. Soc. Chim. France, 1963, 2264–2270. The amine is prepared by reaction of isopropylamine in water with two moles of acrylonitrile at ambient temperature over 4 days in almost quantitative yield. The material is extracted with ether, the ether solution dried over magnesium sulphate and concentrated to a heavy oil. All intermediates are oils and require no further purification.

EXAMPLE 23

When the ethyl carbamate of N-$\beta$-phenethyl-3-cyano-4-amino-$\Delta^3$-piperideine is substituted for the N-methyl compound in Example 20, 2-(2-fluorophenyl)-9-$\beta$-phenethyl-7,8,9,10-tetrahydropyrido[3,4-c][1,2,4]triazolo[1,5-c]pyrimidin-5(6H)one methanesulphonate is obtained, m.p. 167°–171°, in 38% yield.

The ethyl carbamate starting material was prepared in the same manner as the ethyl carbamate in Example 22, except that $\beta$-phenethylamine is substituted for isopropylamine.

EXAMPLE 24

When the ethyl carbamate of 1-benzyl-3-amino-4-cyano-2-methyl-$\Delta^3$-pyrroline is substituted for the ethyl carbamate of the N-benzyl compound in Example 11, 8-benzyl-2-(2-fluorophenyl)-7-methyl-7,9-dihydro-8H-pyrrolo[3,4-c][1,2,4]triazolo[1,5-c]pyrimidin-5(6H)one is obtained, m.p. 290°–293° after recrystallization from 2-methoxyethanol, in 36% yield.

The ethyl carbamate intermediate is prepared from 3-amino-1-benzyl-4-cyano-2-methyl-$\Delta^3$-pyrroline (Cavalla, J. Chem. Soc. 1962, 4664) as described in Example 2.

EXAMPLE 25

A mixture of the ethyl carbamate of 1-amino-2-cyanocyclohept-1-ene (11.6 g), o-fluorobenzhydrazide (8.74 g) and 1-methyl-2-pyrrolidone (140 mL) is stirred at reflux under nitrogen for 18 hours, cooled and triturated with water to produce solid material. It is recrystallized from ($\pm$)1-methoxy-2-propanol to afford pure 2-(2-fluorophenyl)-8,9,10,11-tetrahydro-7H-cyclohepta[e][1,2,4]triazolo-[1,5-c]pyrimidin-5(6H)one, m.p. 257°–259°, in 63% yield.

The starting ethyl carbamate is prepared from 1-amino-2-cyanocyclohept-1-ene (Krüger, J. Organometal. Chem. 9, 125 (1967)) as described in Example 2.

EXAMPLE 26

A mixture of the ethyl carbamate of 4-amino-3-cyanopyridine (1.3 g), o-fluorobenzhydrazide (1.05 g), 2-methoxyethanol (15 mL) and tri-n-propylamine (0.9 mL) is heated at reflux under nitrogen for 66 hours. One-half of the solvent is removed by evaporation at reduced pressure and the mixture is then cooled, filtered and the precipitate washed with ethanol and dried. After one recrystallization from dimethylacetamide-ethanol, it is treated with an equimolar quantity of methanesulphonic acid in methanol and the salt precipitated by addition of ether. The product, (43%) 2-(2-fluorophenyl)-pyrido[3,4-e][1,2,4]triazolo[1,5-c]pyrimidin-5(6H)one methanesulphonate, melts in the range 290° to 293°.

The starting ethyl carbamate is prepared in the following way:

To a heterogeneous mixture of 4-amino-3-cyanopyridine (1.2 g), sodium bicarbonate (1.9 g) and methyl ethyl ketone (30 mL) is added under nitrogen and stirring ethyl chloroformate (1.9 mL). It is refluxed under nitrogen for 20 hours, filtered free of inorganic solid and the filtrate concentrated at reduced pressure. The residual solid is recrystallized from chlorobenzene-cyclohexane to give the desired carbamate, melting in the range 108°–120°. This is suitable for the next step.

EXAMPLE 27

The methyl carbamate of 2-amino-3-cyano-4,5,6,7-tetrahydrobenzo(b)thiophene (7.08 g), 2-fluorobenzhydrazide (4.66 g), 2-methoxyethanol (100 mL) and tri-n-propylamine (3 mL) are refluxed under nitrogen for 19 hours. The mixture is cooled and the precipitate collected. The mother liquor is treated with methanol (100 mL) and refrigerated 24 hours to produce a second crop of solid. The combined material is recrystallized from 2-methoxyethanol and dried 20 hours at 100°/0.01 mm to afford 2-(2-fluorophenyl)-8,9,10,11-tetrahydro[1]benzothieno[3,2-e][1,2,4]triazolo[1,5-c]pyrimidin-5(6H)one, which decomposes above 316°. The yield is 50%.

The starting carbamate is prepared in the following way:

To a solution of 2-amino-3-cyano-4,5,6,7-tetrahydrobenzo[b]thiophene (8.9 g, prepared as described by Gewald et al, Chem. Ber. 99, 94 (1966)), in methyl ethyl ketone (150 mL) is added sodium bicarbonate (5 g) followed by methyl chloroformate (4.2 mL) and the whole stirred at 80° under nitrogen for 20 hours. It is filtered free of inorganic solid while hot and the filtrate concentrated to dryness at reduced pressure. The residue is recrystallized from chlorobenzene-cyclohexane to afford the pure methyl carbamate, m.p. 162°–164°, in 66% yield.

EXAMPLE 28

When the methyl carbamate of 2-amino-3-cyano-4,5-dimethylthiophene is substituted for the carbamate in Example 27, 2-(2-fluorophenyl)-8,9-dimethylthieno[3,2-e][1,2,4]triazolo[1,5-c]pyrimidin-5(6H)one is obtained which decomposes above 330°, in 83% yield.

The starting methyl carbamate is obtained from the aminoitrile (prepared by the method of Gewald et al, loc. cit.) as described in Example 27, m.p. 155°–157° after recrystallization.

EXAMPLE 29

In a pressure vessel is placed 30 mL of ammonium hydroxide saturated with ammonia at 0° and 5-chloro-2(2-furyl)-7,8,9,10-tetrahydro[1,2,4]triazolo[1,5-c]quinazoline (0.63 g) and the whole is heated at 150° for 6 hours. It is cooled and the precipitate collected, washed with methanol and recrystallized from 2-methoxyethanol. The free base is converted with methanesulphonic acid in isopropanol to the salt and precipitated with ether. The pure 5-amino-2(2-furyl)-7,8,9,10-tetrahydro[1,2,4]triazol[1,5-c]quinazoline methaanesulphonate melts in the range 269° to 271°. It is obtained in 38% yield.

The starting chloro compound is prepared as follows:

To a solution of phosphorous pentachloride (0.1 g) in phosphoryl chloride '13.7 mL) is added 2-(2-furyl)-7,8,9,10-tetrahydro[1,2,4]triazolo[1,5-c]quinazolin-5(6H)one (Example 3, 0.64 g), the mixture stirred for 5 minutes and pyridine (0.41 g) added dropwise. It is heated at 110° for 17 hours and then concentrated to dryness at reduced pressure. The residual solid is suspended in ethyl acetate (100 mL) and the mixture washed with cold 2N hydrochloric acid (3×30 mL). The organic layer is dried over sodium sulphate and concentrated to dryness at reduced pressure to a white solid suitable for the next step, in 93% yield.

EXAMPLE 30

A mixture of 3-(5-aminoimidazol-4-yl)-5-phenyl-1,2,4-triazole (11.3 g, from Example 1), methanol (200 mL) and cyanogen bromide (5.25 g) is stirred under nitrogen for 2 hours at 40° C. It is cooled and the solid collected, dissolved in 10N Sodium hydroxide solution, filtered and precipitated by addition of glacial acetic acid to pH 5. The solid is washed with water, stirred in a mixture of methanesulphonic acid in methanol for one-half hour and collected (1.39 g), mp >350°. After drying at room temperature and high vacuum, the hemihydrate of 5-amino-2-phenyl-[1,2,4]triazolo[5,1-i]purine is thus obtained.

EXAMPLE 31

A mixture of 2-(2-fluorophenyl)-7,8,9,10-tetrahydro-[1,2,4]triazolo[1,5-c]quinazolin-5(6H)one, (Example 2, 1.4 g, and sodium methoxide (400 mg) is dissolved in dry dimethyl sulphoxide (80 mL) under nitrogen at 85°, stirred at 50° for 30 minutes and then treated dropwise with methyl iodide (0.7 mL) in dimethylsulphoxide (20 ml). It is allowed to stir another hour at 50°, then quenched in ice-water and the resulting white precipitate collected, washed with water and dried at 100° under vacuum. It is recrystallized from 2-methoxy ethanol to afford pure 2-(2-fluroophenyl)-6-methyl-7,8,9,10-tetrahydro-[1,2,4]-triazolo[1,5-quinazolin-5(6H)one, m.p. 236°–239°.

EXAMPLE 32

To a suspension of 50% sodium hydride in oil (300 mg) in dry dmethylformamide (16 ml) is added 3-(2-aminopyrazin-3-yl)-5-(2-furyl)-1,2,4-triazole (1.37 g) and the whole stirred under nitrogen at 60° until a solution forms. To this is added cyanogen bromide (700 mg) in dimethylformamide (9 ml) and the whole stirred under nitrogen over 66 hours at 60°. It is cooled to 0° and the solid collected, washed with dimethylformamide, then water, then ethanol and finally ether and air dried. It is recrystallized from dimethylacetamide (70 ml) to which methanol (50 ml) is added to form pure 5-amino-(2-furyl)-pyrazino[2,3-e][1,2,4]-triazolo[1,5-c]pyrimidine, melting in the range 347°–351°.

The starting triazole is prepared in the following manner: To a suspension of sodium ethoxide, prepared from sodium (460 mg), in dry ethanol (20 ml) is added 2-furylcarboxamidine hydrochloride (1.9 g) in ethanol (20 ml) under nitrogen and after 5 min. stirring it is filtered and the filtrate added to a mixture of 2-aminopyrazine-3-carbohydrazide (3.1 g), ethanol (10 ml) and chlorobenzene (40 ml). It is heated under nitrogen in an apparatus with a solvent separator at 120° until no more solvent distills, then heated 18 hrs. at reflux. The mixture is cooled, filtered and the solid washed with methanol (3×30 ml) and recrystallized from 2-methoxyethanol to afford the pure triazole m.p. 247°–250°.

The starting hydrazide is prepared by reaction of methyl-2-aminopyrazine-3-carboxylate with hydrazine hydrate at 80° for 1 hr. The methyl ester is prepared by reaction of 2-aminopyrazine-3-carboxylic acid with methanol containing concentrated sulphuric acid over 3 days, m.p. 167°–170°.

EXAMPLE 33

When 2-chlorobenzhydrazide is substituted for p-fluorobenzhydrazide in Example 11, 9-benzyl-2(2-chlorophenyl)-7,8,9,10-tetrahydropyrido[3,4-e][1,2,4]triazolo[1,5-c]pyrimidin-5(6H)one is obtained. It is purified by conversion to the methanesulphonate salt in methanol, m.p. 295°–296°, in 36% overall yield.

EXAMPLE 34

When picolinic acid hydrazide is substituted for p-fluorobenzhydrazide in Example 11, 9-benzyl-2-(2-pyridyl)-7,8,9,10-tetrahydropyrido[3,4-e][1,2,4]triazolo[1,5-c]pyrimidin-5(6H)one is obtained and purified as the methanesulphonate salt, mp. 290°–290°, in 28% overall yield.

EXAMPLE 35

When pyrrole-2-carboxylic acid hydrazide is substituted for p-fluorobenzhydrazide in Example 11, 9-benzyl-2-(2-pyrrolyl)-8,9,10-tetrahydropyrido[3,4-e][1,2,4]triazolo-[1,5-c]pyrimidin-5(6H)one is obtained and purified by trituration in methanol, filtration and drying under reduced pressure. The free base, m.p. 297°–298°, is obtained in 55% yield.

EXAMPLE 36

In a pressure vessel is placed 100 mL of ammonium hydroxide saturated with ammonia at −5° C. and 5-chloro-8,9-dihydro-2(2-furyl)-7H-cyclopenta[e][1,2,4]triazolo-[1,5-c]pyrimidine (1.7 g) dissolved in 1 methyl-2-pyrrolidone (13 mL). It is heated 5.5 hr at an outside temperature of 150° C., then allowed to cool and the solid collected, washed with water and air dried. After two recrystallizations from ethanol, pure 2-(2-furyl)-5-imino-5,6,8,9-tetrahydro-7H-cyclopenta[e][1,2,4]triazolo[1,5-c]-pyrimidine, mp. 255°–260°, is obtained in 49% yield.

EXAMPLE 37

A mixture of the tert-butyl carbamate of 2-amino-3-cyanopyridine (4.6 g), 2-furoylhydrazine (2.65 g) and 1-methyl-2-pyrrolidone (46 mL) is heated at 160° over 18 hr. It is cooled and diluted with water (369 mL) to afford 2-(2-furyl)pyrido-[3,2-e][1,2,4]-triazolo[1,5-c]pyrimidin-5(6H)one in 53% yield. It is purified by tituration in hot methanol, which removes the soluble impurities, and melts above 360° C.

The starting urethane is prepared in the following way: The tert-butyl carbamate of 2-aminopyridine (9.6 g) is treated dropwise under nitrogen in ether (980 mL) at −78° C. with tert-butyl lithium in pentane (1.55 Molar, 70.19 mL). It is stirred at room temperature for 2 hr., recooled to −78° and a solution of p-toluenesulphonyl cyanide (9.84 g) in either (98 mL) added dropwise under nitrogen. The mixture is stirred at room temperature over 18 hr., treated with brine (400 mL) and extracted with ether. The ether extract is dried over magnesium sulphate, concentrated to dryness at reduced pressure and the residual solid recrystallized from 1:1 ether-petroleum-ether to afford the desired urethane in 43% yield.

The tert-butyl urethane of 2-aminopyridine is prepared by reaction of equimolar quantities of 2-aminopyridine and di-tert-butyl carbonate at reflux 2 hr. then at ambient temperature for 18 hr. The mixture is filtered to remove white solid and the filtrate evaporated to dryness at reduced pressure, taken up in hot ethanol, diluted with water and cooled whereupon the urethane crystallizes in 45% yield, mp. 93°–94°.

EXAMPLE 38

To a solution of sodium hydride (0.75 g) in dimethylformamide (79.6 mL) is added 3-(2-aminopyrid-3-yl)-5-(2-furyl) 1,2,4-triazol (6.8 g) and the whole stirred at 60° C. under nitrogen until a solution forms. Cyanogen bromide (3.48 g) is added and the whole stirred at 60° for 66 hrs. The mixture is cooled, and the solid collected, washed with dimethylformamide and then water. The filtrate is further diluted with water to form a second crop of product. The combined solid is suspended in water, and 5N sodium hydroxide added to adjust the pH to 10. After 30 minutes the solid is collected, washed well with water and air dried. The solid is suspended in warm methanol (60 mL), treated with an equimolar quantity of methane sulphonic acid, filtered and concentrated to one-third volume. The product, 5,6-dihydro-2-(2-furyl)-5-iminopyrido[3,2-e][1,2,4]triazolo[1,5-c]-pyrimidine methanesulphonate obtained in 10% yield, melts in the range 330° to 332° C.

The triazole starting material is prepared in the following way:

The product of Example 37 (10.1 g) and sodium hydroxide (3.19 g) in water (398 mL) is stirred at reflux over 18 hr., filtered hot and the filtrate cooled and adjusted to pH 7 with 2N hydrochloric acid. The precipitated solid (6.87 g) is collected and dried. The material is suitable for further work but can be purified as methanesulphonate salt, mp. 242°–244°.

EXAMPLE 39

When the tert-butyl carbamate of 3-amino-4-cyanopyridine replaces the urethane described in Example 37 and o-fluorobenzhydrazide replaces 2-furoylhydrazine in the same example, 2-(2-fluorophenyl)-pyrido[4,3-e][1,2,4]triazolo[1,5-c]pyrimidin-5(6H)one is obtained in 78% yield, m.p. 324°–326°. It is purified as the membrane sulphonate salt, m.p. 285° to 287°.

The tert-butylcarbamate of 3-amino-4-cyanopyridine, obtained in 31% yield, mp. 100°–103° is obtained from the tert-butyl carbamate of 3-aminopyridine, mp. 105°–109°, as described in Example 37.

EXAMPLE 40

When the tert-butyl carbamate of 4-amino-3-cyanopyridine replaces the carbamate of 2-amino-3-cyanopyridine in Example 37, 2-(2-furyl)pyrido[3,4-e][1,2,4]triazolo[1,5-c]pyrimidin-5(6H)one is obtained in 26% yield. It is characterized as the methane sulphonate salt, mp. 312° to 313°.

The tert-butyl carbamate of 4-amino-3-cyanopyridine is prepared from the carbamate of 4-aminopyridine (Fishwick et al, J.C.S. Chem. Comm. 1984, 1304) in 42% yield as described in Example 37.

EXAMPLE 41

When 3-(4-aminopyrid-3-yl)-5-(2-furyl)-1,2,4-triazole replaces the triazole in Example 38, 5,6-dihydro-2-(2-furyl)5-imino-pyrido[3,4-e][1,2,4]triazolo[1,5-c]pyrimidine is obtained in 39% yield and characterized as the methane sulphonate salt, mp. 320° to 321°.

The starting triazole, is obtained in 66% yield from the compound of Example 40 as described in Example 38.

EXAMPLE 42

A mixture of the product of Example 15 (570 mg), ethyl bromoacetate (8 mL) and dry dimethylformamide (15 mL) is stirred at 100° C. under nitrogen for 1.5 hr. It is poured into cold 8% aqueous sodium bicarbonate and stirred vigorously to form crystals. The solid is collected, washed with water (2×20 mL), then ether (2×30 mL) and recrystallized from ethanol to afford pure 9-carbomethoxymethyl-2-(2-fluorophenyl)-7,8,9,10-tetrahydropyrido[3,4-e][1,2,4]triazolo[1,5-c]pyrimidin-5(6H)one, m.p. 265°–266°.

EXAMPLE 43

To a suspension of the product of Example 15 (280 mg), 3-picolyl chloride hydrochloride (197 mg) and dry dimethylformamide (10 mL) under nitrogen is added triethylamine (0.4 mL) under stirring and the whole stirred at ambient temperature over 94 hours. It is quenched in cold 5% aqueous sodium hydroxide, whereupon crystals gradually form from solution. The product is washed with ice-water (2×5 mL), then ether (2×10 mL) and treated with twice the equimolar amount of methanesulphonic acid in methanol (10 mL). The resulting white crystalline product is collected, washed with ether (2×5 mL) and dried in vacuo to give pure 2-(2-fluorophenyl)-9-(3-picolyl)-7,8,9,10,11,12-hexahydrocycloocta[e][1,2,4]triazolo[1,5-c]pyrimidin-5(6H)one.

EXAMPLES 44 AND 45

By the route described in Example 43, 2(2-fluorophenyl)-9-(2-picolyl)-7,8,9,10-tetrahydro[3,4-c][1,2,4]triazolo[1,5-c]pyrimidin-5(6H)one dimethanesulphonate is obtained from 2-picolyl chloride hydrochloride and the corresponding 4-picolyl compound is prepared from 4-picolyl chloride hydrochloride.

EXAMPLE 46

By a route similar to that described in Example 43, the product from Example 15 is reacted with benzene sulphonyl chloride to give 2-(2-fluorophenyl)-9-phenylsulphonyl-7,8,9,10-tetrahydropyrido[3,4-e][1,2,4]triazolo[1,5-c]pyrimidin-5(6H)one.

EXAMPLE 47

To a suspension of the product of Example 42 (500 mg) in ethanol (20 mL) is added 4N aqueous sodium hydroxide (1 mL) and the whole stirred at reflux under nitrogen for 2 hours. It is cooled, filtered and the filtrate neutralized with glacial acetic acid with ice cooling to produce the solid 9-carboxymethyl-2-(2-fluorophenyl)-7,8,9,10-tetrahydropyrido[3,4-e][(1,2,4]triazolo[1,5-c]pyrimidin-5(6H)one.

EXAMPLE 48

The product of Example 47 (500 mg) is stirred in thionyl chloride (5 mL) over 4 hours and then concentrated to dryness at reduced pressure. The residual material is treated with a cold saturated solution of ammonia in methanol (50 mL) and, after overnight stirring, the mixture is diluted with water and the product, 9-carbamoylmethyl-2-(2-fluorophenyl)-7,8,9,10-tetrahydropyrido[3,4-e][(1,2,4]-triazolo[1,5-c]pyrimidin-5(6H)one, collected and recrystallized from dimethylacetamide-water.

EXAMPLE 49

To a solution of the product of Example 15 (570 mg) in 1:1 glacial acetic acid-water is added potassium cyanate (324 mg) in water (3 mL) under stirring at 35° C. After 2 hours, it is heated briefly to 80°, cooled, diluted with water and the product, 9-carbamoyl-2-(2-fluorophenyl)-7,8,9,10-tetrahydropyrido[3,4-e][1,2,4]triazolo[1,5-c]pyrimidin-5(6H)one, collected, washed with water and purified by recrystallization from dimethylacetamide-water.

EXAMPLE 50

A mixture of the product of Example 15 (570 mg), bromoacetonitrile (360 mg), dimethylformamide (10 mL) and triethylamine (0.5 mL) is stirred under nitrogen over 4 days. It is poured into 10% aqueous sodium bicarbonate and stirred vigorously over ½ hour. The material is collected, washed with water, then ether and dried in vacuo to afford 9-cyanomethyl-2-(2-fluorophenyl)-7,8,9,10-tetrahydropyrido[3,4-e][1,2,4]triazolo[1,5-c]pyrimidin-5(6H)one.

EXAMPLE 51

A mixture of the product of Example 50 (640 mg), sodium azide (1.41 g), ammonium chloride (120 mg) and dimethylformamide (10 mL) is stirred at 90° over 3 hours under nitrogen. The mixture is cooled and quenched in ice-water (40 mL), stirred ½ hour, and cautiously acidified with glacial acetic acid to afford the solid product 2-(2-fluorophenyl)-9-tetrazolylmethyl-7,8,9,10-tetrahydropyrido[3,4-e][1,2,4]triazolo[1,5-c]pyrimidine-5(6H)one.

EXAMPLES 52 AND 53

When the ethylcarbamate of N-benzyl-3-cyano-4-amino-Δ³-piperideine of Example 8 is replaced by the ethyl carbamate of (+) or (−) N-alpha-methylbenzyl-3-cyano-4-amino-Δ³-piperideine, the corresponding (+) or (−) 2-(2-fluoro)-9-alpha-methylbenzyl)-7,8,9,10-tetrahydropyrido[3,4-e][1,2,4]triazolo-[1,5-c]pyrimidin-5(6H)one is obtained.

What is claimed is:

1. A 2-substituted-e-fused[1,2,4]-triazolo[1,5-c]pyrimidine compound of the formula

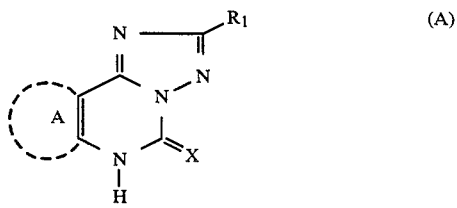

(A)

a tautomer thereof or a pharmaceutically acceptable salt of said compound or tautomer, wherein
X is oxygen;
R₁ is selected from
(a) phenyl which is unsubstituted or substituted by lower alkyl, lower alkoxy, hydroxy, or halogen;
(b) furyl, thienyl, pyridyl, pyrrolyl, and thiazolyl, each of which is unsubstituted or substituted by lower alkyl, lower alkoxy, hydroxy, hydroxy-lower alkyl, halogen, or amino; and
(c) β-D-ribofuranosyl;
ring A being selected from cyclohexene, cycloheptene, pyridine, tetrahydropyridine, pyrazine, pyrimidine and imidazole, each ring A being unsubstituted or substituted by a substituent selected from lower alkyl, lower alkoxy, hydroxy, halogen, halo-lower alkyl, nitro, amino, carbamoyl, lower alkoxy-carbamoyl, lower alkylthio, lower alkylsulfinyl, lower alkylsulfonyl, phenyl-lower alkyl, and benzoyl.

2. The compound of claim 1 wherein R₁ is (a) phenyl which is unsubstituted or substituted by lower alkyl, lower alkoxy, or halogen; or (b) furyl, pyridyl, pyrrolyl, or thiazolyl which is mono or disubstituted by lower alkyl, lower alkoxy, hydroxy, hydroxy lower alkyl, halogen, or amino; or (c) β-D-ribofuranosyl; a tautomer thereof or a salt of said compound or said tautomer.

3. The compound of claim 1 wherein R₁ is selected from phenyl, halophenyl, furyl, pyridyl, pyrrolyl, and β-D-ribofuranosyl; a tautomer thereof, or a pharmaceutically acceptable salt of said compound or said tautomer.

4. The compound of claim 3 wherein R₁ is selected from 2-chlorophenyl, 2-fluorophenyl, 2-pyridyl, 2-pyrrolyl, and 2-furyl; a tautomer thereof or a pharmaceutically acceptable salt of said compound or said tautomer.

5. The methane sulfonate salt of a compound of claim 1 or a tautomer thereof.

6. The compound of claim 1 wherein said phenyl of R₁ is phenyl which is substituted by one to three groups selected from lower alkyl, lower alkoxy, hydroxy, and halogen; a tautomer thereof, or a pharmaceutically acceptable salt of said compound or said tautomer.

7. The compound of claim 1 wherein said R₁ furyl is 2-furyl or 3-furyl; said R₁ thienyl is 2-thienyl or 3-thienyl; said R₁ pyridyl is 2-pyridyl, 3-pyridyl, or 4-pyridyl; said R₁ pyrrolyl is 2-pyrrolyl or 3-pyrrolyl; each of the foregoing R₁ groups being unsubstituted or substituted by lower alkyl, hydroxy, or halogen; a tautomer thereof or a pharmaceutically acceptable salt of said compound or said tautomer.

8. The compound of claim 1 wherein said R₁ phenyl is unsubstituted or substituted in the ortho or meta position by fluorine or chlorine; a tautomer thereof or a pharmaceutically acceptable salt thereof or of said tautomer.

9. The compound, tautomer, or pharmaceutically acceptable salt of claim 1 wherein said ring A substituent is selected from phenyl-lower alkyl and carbamoyl.

10. The compound, tautomer, or pharmaceutically acceptable salt of claim 9 wherein said ring A is unsubstituted or substituted by a substituent selected from benzyl, 1-phenethyl, and carbamoyl.

11. The compound, tautomer, or pharmaceutically acceptable salt of claim 1 wherein ring A is selected from pyridine, pyrazine, pyrimidine, tetrahydropyridine, and imidazole, each of which is unsubstituted or substituted as in claim 1.

12. The compound, tautomer, or pharmaceutically acceptable salt of claim 11 ring A is tetrahydropyridine piperideine, or pyridine which is unsubstituted or substituted as in claim 11.

13. The compound, tautomer or pharmaceutically acceptable salt of claim 12 wherein ring A is 1,2,5,6- or 1,2,3,6-tetrahydropyridine or pyridine fused to the pyrimidine ring of formula A at the b, c, d, or e face of said pyridine ring A, which is unsubstituted or substituted as in claim 12.

14. The compound, tautomer or pharmaceutically acceptable salt of claim 13 wherein said ring A is 1,2,5,6-tetrohydropyridine or pyridine fused to the pyrimidine ring of formula A at the c or d face of said pyridine ring A, each of which is unsubstituted or substituted as in claim 13.

15. The compound of claim 1 wherein
(a) R₁ is o-fluorophenyl and ring A is cycloheptene-1,2-diyl;
(b) R₁ is phenyl, 2-halophenyl, 2-pyridyl, 2-pyrrolyl, 2-furyl, and ring A is N-benzyl-(1,2,5,6 or 1,2,3,6)-tetrahydropyridin-3,4-dioyl or b, c, d, or e fused pyridine;
a tautomer thereof or a pharmaceutically acceptable salt of said compound or said tautomer.

16. A compound of claim 1 selected from
9-benzyl-2-(2-chlorophenyl)-7,8,9.10-tetrahydropyrido-[3,4-e][1,2,4]triazolo[1,5-c]pyrimidine-5(6H)-one;
9-benzyl-2-(2-pyridyl)-7,8,9,10-tetrahydropyrido[3,4-e] [1,2,4]triazolo[1,5-c]pyrimidin-5(6H)-one;
2-(2-furyl)-pyrido[3,2-e][1,2,4]triazolo[1,5-c]pyrimidin-5(6H)-one;
2-(2-fluorophenyl)-pyrido[4,3-e][1,2,4]triazolo[1,5-c]pyrimidin-5(6H)-one; and
2-(2-furyl)-pyrido[3,4-e][1,2,4]triazolo[1,5-c]pyrimidin-5(6H)-one;
a tautomer thereof or a pharmaceutically acceptable salt of said compound or tautomer.

17. The compound of claim 1 wherein R₁ is o-fluorophenyl and ring A is cyclohepten-1,2-diyl, a tautomer thereof or a pharmaceutically acceptable salt of said compound or said tautomer.

18. A compound of the formula

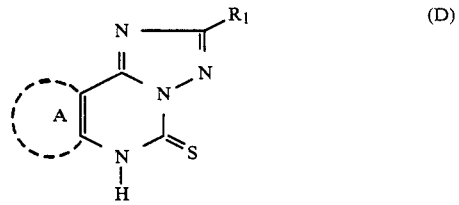

(D)

a tautomer thereof or a pharmaceutically acceptable salt of said compound or tautomer wherein
R₁ is selected from
(a) phenyl which is unsubstituted or substituted by lower alkyl, lower alkoxy, hydroxy, or halogen;
(b) furyl, thienyl, pyridyl, pyrrolyl, and thiazolyl, each of which is unsubstituted or substituted by lower alkyl, lower alkoxy, hydroxy, hydroxy-lower alkyl, halogen, or amino; and
(c) β-D-ribofuranosyl;
ring A being selected from tetrahydropyridine, pyridine, pyrazine, pyrimidine, and imidazole, each of which is unsubstituted or substituted by a substituent from lower alkyl, lower alkoxy, hydroxy, halogen, halo-lower alkyl, nitro, amino, carbamoyl, lower alkoxycarbonyl, lower alkylthio, lower alkylsulfinyl, lower alkylsulfonyl, phenyl-lower alkyl, and benzoyl.

19. A compound of the formula

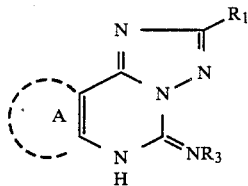

a tautomer thereof or a pharmaceutically acceptable salt of said compound or said tautomer wherein $R_1$ is selected from
(a) phenyl which is unsubstituted or substituted by lower alkyl, lower alkoxy, hydroxy, or halogen; and
(b) furyl, thienyl, pyridyl, pyrrolyl, or thiazolyl, each of which is unsubstituted or substituted by lower alkyl, lower alkoxy, hydroxy, hydroxy-lower alkyl, halogen, or amino; and
(c) β-D-ribofuranosyl;

ring A being selected from tetrahydropyridine, pyridine, pyrazine, pyrimidine, and imidazole; each ring A being unsubstituted or substituted by a substituent selected from lower alkyl, lower alkoxy, hydroxy, halogen, halo-lower alkyl, nitro, amino, carbamoyl, lower alkoxy carbonyl, lower alkyl thio, lower alkyl sulfinyl, lower alkyl sulfonyl, aryl lower alkyl, and aryl carbonyl,; wherein said aryl portion is phenyl;

$R_3$ is selected from hydrogen, lower alkyl, lower alkenyl, and lower alkynyl.

20. The compound of claim 19 wherein $R_1$ is (a) phenyl which is unsubstituted or substituted by lower alkyl, lower alkoxy, or halogen; or (b) furyl, pyridyl, pyrrolyl, or thiazolyl which is mono or disubstituted by lower alkyl, lower alkoxy, hydroxy, hydroxy lower alkyl, halogen, or amino; or (c) β-D-ribofuranosyl; a tautomer thereof or a salt of said compound or said tautomer.

21. The compound of claim 19 wherein $R_1$ is selected from phenyl, halophenyl, furyl, pyridyl, pyrrolyl, and β-D-ribofuranosyl; a tautomer thereof, or a pharmaceutically acceptable salt of said compound or said tautomer.

22. The compound of claim 21 wherein $R_1$ is selected from 2-chlorophenyl, 2-fluorophenyl, 2-pyridyl, 2-pyrrolyl, and 2-furyl; a tautomer thereof or a pharmaceutically acceptable salt of said compound or said tautomer.

23. The methane sulfonate salt of a compound of claim 19 or a tautomer thereof.

24. The compound of claim 19 wherein said phenyl of $R_1$ is phenyl which is substituted by one to three groups selected from lower alkyl, lower alkoxy, hydroxy, and halogen; a tautomer thereof, or a pharmaceutically acceptable salt of said compound or said tautomer.

25. The compound of claim 19 wherein $R_1$ furyl is 2-furyl or 3-furyl; said $R_1$ is thienyl is 2-thienyl or 3-thienyl; said $R_1$ pyridyl is 2-pyridyl, 3-pyridyl, or 4-pyridyl; said $R_1$ is pyrrolyl is 2-pyrrolyl or 3-pyrrolyl; each of the foregoing $R_1$ groups being unsubstituted or substituted by lower alkyl, hydroxy, or halogen; a tautomer thereof or a pharmaceutically acceptable salt of said compound or said tautomer.

26. The compound of claim 19 wherein said $R_1$ phenyl is unsubstituted or substituted in the ortho or meta position by fluorine or chlorine; a tautomer thereof or a pharmaceutically acceptable salt thereof or of said tautomer.

27. The compound, tautomer or pharmaceutically acceptable salt of claim 19 wherein said ring A substituent is selected from, aryl lower alkyl, carboxy lower alkyl, and carbamoyl, in which said aryl is phenyl.

28. The compound, tautomer, or pharmaceutically acceptable salt of claim 27 wherein said ring A is unsubstituted or substituted by a substituent selected from benzyl, 1-phenethyl, and carbamoyl.

29. The compound of claim 19 wherein $R_1$ is 2-furyl and ring A is
(a) 2-, 3-, or 4-pyridyl,
(b) the tetrahydro analogs of 'a' in which the side fused to the pyrimidine ring is a double bond, or
(c) imidazolyl each of which is unsubstituted or substituted as in claim 19; a tautomer thereof or a pharmaceutically acceptable salt of said compound or said tautomer.

30. The compound of claim 29 wherein said ring A is 1,2,5,6-tetrahydropyridine, 2-pyridyl or imidazolyl, each of which is unsubstituted or substituted by lower alkyl; a tautomer thereof or a pharmaceutically acceptable salt of said compound or said tautomer.

31. The compound, tautomer, or pharmaceutically acceptable salt of claim 19 wherein ring A is selected from tetrahydropyridine pyridine, pyrazine, pyrimidine and imidazole, each of which is unsubstituted or substituted as in claim 19.

32. The compound, tautomer, or pharmaceutically acceptable salt of claim 31 ring A is tetrahydropyridine or pyridine which is unsubstituted or substituted as in claim 31.

33. The compound, tautomer or pharmaceutically acceptable salt of claim 32, wherein ring A is 1,2,5,6-tetrahydropyridine or pyridine fused to the pyrimidine ring of formula A at the b, c, d, or e face of said pyridine ring A, which is unsubstituted or substituted as in claim 32.

34. The compound, tautomer or pharmaceutically acceptable salt of claim 33 wherein said ring A is 1,2,5 6-tetrahydropyridine or pyridine fused to the pyrimidine ring of formula A at the c or d face of said pyridine ring A, each of which is unsubstituted or substituted as in claim 33.

35. The compound of claim 19 wherein $R_1$ is 2-furyl and ring A is cyclopenten-1,2-diyl, cyclohexen-1,2-diyl, or pyridyl, a tautomer thereof or a pharmaceutically acceptable salt of said compound or said tautomer.

36. The compound of claim 19 wherein $R_3$ is lower alkyl, a tautomer thereof or a pharmaceutically acceptable salt of said compound or said tautomer.

37. The compound of claim 19 selected from
2-(2-furyl)-5-imino-5,6,7,8,9,10-hexahydro-[1,2,4]triazolo-[1,5-c]-pyrimidine;
5,6-dihydro-2-(2-furyl)-5-imino-pyrido[3,2-e][1,2,4]triazolo[1,5-c]pyrimidine; and
5,6-dihydro-2-(2-furyl)-5-imino-pyrido[4,3,-e][1,2,4]l triazolo[1,5-c]pyrimidine;

a tautomer thereof or a pharmaceutically acceptable salt of said compound or said tautomer.

38. A method of counteracting the effects of a benzodiazepine comprising administering to a mammal in need of such administration a benzodiazepine antagonistically effective amount of a benzodiazepine antagonistic compound of claim 1.

39. A method of reducing anxiety comprising administering to a mammal in need of such administration an anxiolytically effective amount of an anxiolytic compound of claim 1.

40. A method of counteracting the effects of adenosine comprising administering to a mammal in need of such administration an adenosine antagonistically effective amount of an adenosine antagonistic compound of claim 19.

41. A method of treating asthma comprising administering to a mammal in need of such administration an anti-asthmatic effective amount of an antiasthmatic compound of claim 19.

42. A pharmaceutical composition for counteracting the effects of benzodiazepine comprising a benzodiazepine antagonistic effective amount of a benzodiazepine antagonistic compound of claim 1 and a pharmaceutically acceptable carrier.

43. A pharmaceutical composition for treating anxiety comprising an antianxiety effective amount of anxiolytic compound of claim 1 and a pharmaceutically acceptable carrier.

44. A pharmaceutical composition for counteracting the effects of adenosine comprising an adenosine antagonistic effective amount of an adenosine antagonistic compound of claim 19 and a pharmaceutically acceptable carrier.

45. A pharmaceutical composition for the treatment of asthma comprising an anti-asthmatic effective amount of an anti-asthmatic compound of claim 19 and a pharmaceutically acceptable carrier.

* * * * *

UNITED STATES PATENT AND TRADEMARK OFFICE
CERTIFICATE OF CORRECTION

PATENT NO. : 4,831,013
DATED : May 16, 1989
INVENTOR(S) : John E. Francis It is certified that error appears in the above-identified patent and that said Letters Patent is hereby corrected as shown below:

In the Claims:

In claim 12, column 30, line 3, delete "piperideine"

In claim 14, column 30, line 13, "1,2,5,6-tetrohydropyridine" should read ---1,2,5,6-tetrahydropyridine---.

In claim 18, column 31, line 1, after "substituent", insert ---selected---.

In claim 25, column 31, line 66, delete "is" (first occurrence)

In claim 27, column 32, line 10-11, delete "carboxy lower alkyl".

In claim 37, column 32, line 63, "5,6-dihydro-2-(2-furyl)-5-imino-pyrido[4,3,-e][1,2,4]1" should read:
---5,6-dihydro-2-(2-furyl)-5-imino-pyrido [4,3,-e][1,2,4]- ---.

Signed and Sealed this

Eighth Day of May, 1990

*Attest:*

HARRY F. MANBECK, JR.

*Attesting Officer*    *Commissioner of Patents and Trademarks*